US012059546B2

(12) United States Patent
Vaz et al.

(10) Patent No.: US 12,059,546 B2
(45) Date of Patent: Aug. 13, 2024

(54) METHODS AND SYSTEMS FOR ADAPTIVE TIMING OF A SECOND CONTRAST BOLUS

(71) Applicant: GE Precision Healthcare LLC, Milwaukee, WI (US)

(72) Inventors: Michael Sarju Vaz, Milwaukee, WI (US); Bradley Gabrielse, Brookfield, WI (US); Chelsey Lewis, Waukesha, WI (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 1016 days.

(21) Appl. No.: 17/010,497

(22) Filed: Sep. 2, 2020

(65) Prior Publication Data

US 2021/0128820 A1     May 6, 2021

Related U.S. Application Data

(63) Continuation-in-part of application No. 16/672,261, filed on Nov. 1, 2019, now Pat. No. 11,690,950.

(51) Int. Cl.
*A61M 5/00* (2006.01)
*A61B 6/00* (2024.01)
(Continued)

(52) U.S. Cl.
CPC ............ *A61M 5/007* (2013.01); *A61B 6/481* (2013.01); *A61B 6/504* (2013.01); *A61M 5/1723* (2013.01);
(Continued)

(58) Field of Classification Search
CPC ... A61M 5/007; A61M 2205/50; A61B 6/032; A61B 6/4208; A61B 6/481; A61B 6/486;
(Continued)

(56) References Cited

U.S. PATENT DOCUMENTS 5,400,378 A    3/1995 Toth
6,023,494 A    2/2000 Senzig et al.
(Continued)

FOREIGN PATENT DOCUMENTS

CN     101277648 A    10/2008

OTHER PUBLICATIONS

Mitsui et al. 2018 ECR 2018 European Society of Radiology Poster C-1424 EPOS electronic Presentation Online System 28 pages; Pub.Date Mar. 2019 (Year: 2019).*
(Continued)

*Primary Examiner* — Keith M Raymond
*Assistant Examiner* — Patrick M Mehl
(74) *Attorney, Agent, or Firm* — McCoy Russell LLP

(57) ABSTRACT

Methods and systems are provided for adaptive scan control. In one embodiment, a method includes, upon a first contrast injection of a first contrast bolus, processing acquired projection data of a subject to measure a contrast signal of the first contrast bolus, setting a timing for a second contrast injection of a second contrast bolus to a fallback injection timing, and responsive to identifying an adaptive injection timing for the second contrast injection based on the contrast signal before the fallback injection timing is reached, updating the timing for the second contrast injection to the adaptive injection timing and commanding initiation of the second contrast injection at the adaptive injection timing, otherwise commanding initiation of the second contrast injection at the fallback injection timing.

20 Claims, 11 Drawing Sheets

(51) Int. Cl.

| | | |
|---|---|---|
| *A61B 6/46* | (2024.01) | |
| *A61B 6/50* | (2024.01) | |
| *A61M 5/172* | (2006.01) | |
| *G06N 20/00* | (2019.01) | |
| *G06T 7/11* | (2017.01) | |
| *G06T 7/174* | (2017.01) | |
| *G16H 30/40* | (2018.01) | |
| *G16H 40/40* | (2018.01) | |
| *G16H 40/63* | (2018.01) | |
| *G16H 50/20* | (2018.01) | |
| *G16H 50/30* | (2018.01) | |
| *G16H 50/70* | (2018.01) | |

(52) U.S. Cl.
CPC ............... *G06N 20/00* (2019.01); *G06T 7/11* (2017.01); *G06T 7/174* (2017.01); *G16H 30/40* (2018.01); *G16H 40/40* (2018.01); *G16H 40/63* (2018.01); *G16H 50/20* (2018.01); *G16H 50/30* (2018.01); *G16H 50/70* (2018.01); *A61B 6/469* (2013.01); *G06T 2207/10081* (2013.01)

(58) Field of Classification Search
CPC ......... A61B 6/507; A61B 6/542; A61B 6/545; G06T 7/0016; G06T 7/11; G06T 2207/10081; G06T 2207/20081; G06T 2207/20084; G06T 2207/30104
See application file for complete search history.

(56) References Cited

U.S. PATENT DOCUMENTS

| | | |
|---|---|---|
| 6,236,706 B1 | 5/2001 | Hsieh |
| 6,256,368 B1 | 7/2001 | Hsieh et al. |
| 6,891,918 B2 | 5/2005 | Drummond et al. |
| 7,145,982 B2 | 12/2006 | Keda et al. |
| 7,983,460 B2 | 7/2011 | Licato et al. |
| 9,327,143 B2 | 5/2016 | Gillece et al. |
| 9,486,176 B2 | 11/2016 | Goyal |
| 9,517,042 B2 | 12/2016 | Hsieh et al. |
| 9,622,717 B2 | 4/2017 | Londt et al. |
| 10,349,909 B2 | 7/2019 | Okerlund et al. |
| 2013/0109966 A1* | 5/2013 | Assmann ............... A61B 6/481 600/431 |
| 2017/0086772 A1 | 3/2017 | Vaz et al. |
| 2017/0209113 A1 | 7/2017 | Jackson et al. |
| 2018/0049714 A1 | 2/2018 | Nett |
| 2018/0168529 A1* | 6/2018 | Rauch ................... A61B 6/481 |
| 2019/0231288 A1 | 8/2019 | Profio et al. |
| 2019/0313990 A1* | 10/2019 | Sahbaee Bagherzadeh ................ A61B 6/507 |

OTHER PUBLICATIONS

"The ONE Guides—4D Neurological Imaging," Cannon Medical Systems USA Website, Available Online at https://us.medical.canon/download/aq-one-club-guide-4d-neuro-imaging, Available Online at Early as Jan. 2010, 16 pages.

Hinzpeter, R. et al., "CT Angiography of the Aorta: Contrast Timing by Using a Fixed versus a Patient-specific Trigger Delay," University of Zurich Open Repository and Archive Website, Available Online at https://www.zora.uzh.ch/id/eprint/170529/1/radiol.2019182223.pdf, Available as Early as May 2019, 10 pages.

Lewis, C. et al., "Methods and Sytems for Protocol Management," U.S. Appl. No. 16/553,028, filed Aug. 27, 2019, 59 pages.

Vaz, M. et al., "Methods and Systems for Timing a Second Contrast Bolus," U.S. Appl. No. 16/672,261, filed Nov. 1, 2019, 84 pages.

Vaz, M. et al., "Methods and Systems for an Adaptive Multi-Phase Angiography Scan," U.S. Appl. No. 16/672,281, filed Nov. 1, 2019, 85 pages.

Vaz, M. et al., "Methods and Systems for an Adaptive Five-Zone Perfusion Scan," U.S. Appl. No. 16/672,314, filed Nov. 1, 2019, 85 pages.

Vaz, M. et al., "Methods and Systems for a Single-Bolus Angiography and Perfusion Scan," U.S. Appl. No. 16/672,336, filed Nov. 1, 2019, 85 pages.

Vaz, M. et al., "Methods and Systems for an Adaptive Four-Zone Perfusion Scan," U.S. Appl. No. 16/672,350, filed Nov. 1, 2019, 85 pages.

Vaz, M. et al., "Methods and Systems for an Adaptive Perfusion Scan," U.S. Appl. No. 16/698,291, filed Nov. 27, 2019, 43 pages.

* cited by examiner

FIG. 13

METHODS AND SYSTEMS FOR ADAPTIVE TIMING OF A SECOND CONTRAST BOLUS

RELATED APPLICATIONS

The present application is a continuation-in-part of U.S. application Ser. No. 16/672,261, entitled "METHODS AND SYSTEMS FOR TIMING A SECOND CONTRAST BOLUS" and filed on Nov. 1, 2019, the entire contents of which are hereby incorporated by reference for all purposes.

FIELD

Embodiments of the subject matter disclosed herein relate to non-invasive diagnostic imaging, and more particularly, to real-time adaptive contrast imaging.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

For emergency room (ER) stroke management, time is critical to determine a proper course of treatment. For every minute a large vessel ischemic stroke is untreated, the average patient loses 1.9 million neurons. For each hour in which a treatment fails, the patient loses as many neurons as it does in almost 3.6 years of normal aging. Current standards of care require two contrast boli for separate CT angiography (CTA) and CT perfusion (CTP) studies. Further, prior to performing CTA and CTP studies, typical methods first perform a timing bolus scan, wherein a small contrast bolus is administered to a patient and subsequent contrast levels within the patient are monitored to generate a CTP/CTA scan prescription personalized to the patient. However, the timing bolus scan alone takes five minutes, and performing CTA and CTP studies separately requires five to seven minutes between acquisitions to allow contrast washout.

BRIEF DESCRIPTION

In one embodiment, a method includes, upon a first contrast injection of a first contrast bolus, processing acquired projection data of a subject to measure a contrast signal of the first contrast bolus, setting a timing for a second contrast injection of a second contrast bolus to a fallback injection timing, and responsive to identifying an adaptive injection timing for the second contrast injection based on the contrast signal before the fallback injection timing is reached, updating the timing for the second contrast injection to the adaptive injection timing and commanding initiation of the second contrast injection at the adaptive injection timing, otherwise commanding initiation of the second contrast injection at the fallback injection timing.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 13 shows an example of an adaptive scan protocol GUI;

DETAILED DESCRIPTION

Figure 1:
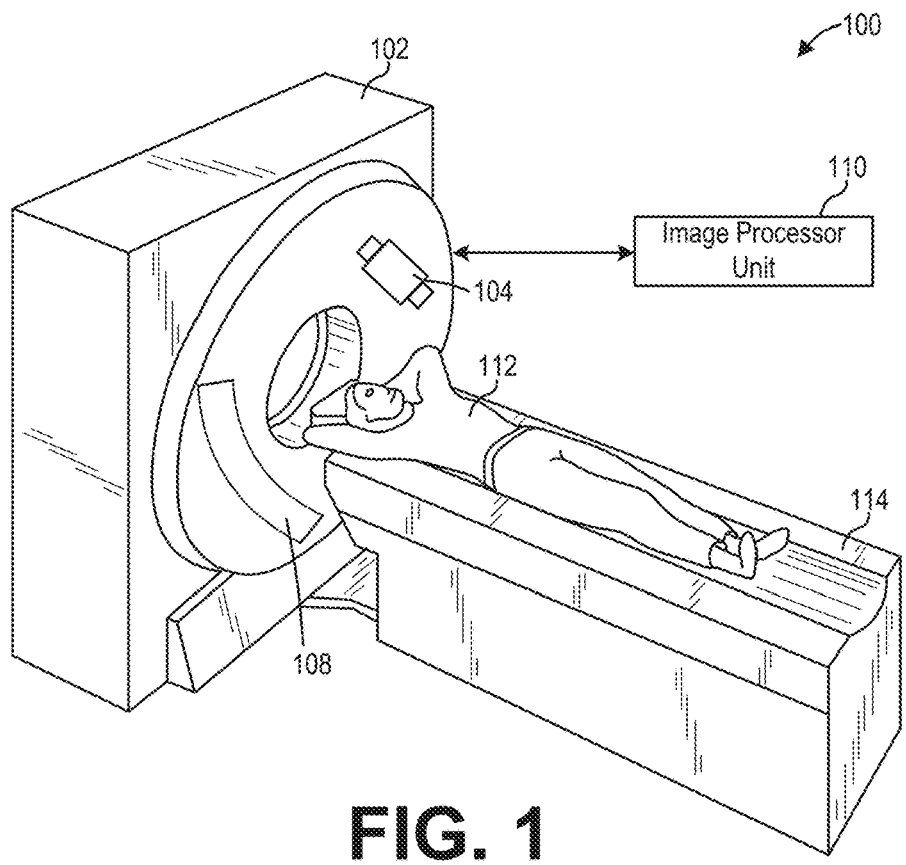
FIG. 1 shows a pictorial view of an imaging system, according to an embodiment.

Some diagnostic imaging protocols, such as protocols to diagnose acute stroke in a patient, include one or more contrast scans, where a contrast agent is administered to the patient prior to the diagnostic imaging scan. These diagnostic imaging protocols may include two contrast scans, such as a computed tomography (CT) angiography (CTA) scan followed by a CT perfusion (CTP) scan. In a CTA followed by a CTP (or in a CTP followed by a CTA), the decision of when to administer the second contrast agent bolus may be challenging, and if timed incorrectly, may result in non-diagnostic images and/or undesired patient outcomes. For example, if the second contrast agent bolus is administered too soon after the first contrast agent bolus, diagnostic image quality of images acquired during the second contrast scan may be degraded due to venous contrast contamination from the first contrast agent bolus. However, if the second contrast agent bolus is administered too late after the first contrast agent bolus, patient outcome (e.g., life expectancy, quality of life) may be impacted.

Thus, according to embodiments disclosed herein, the timing of a second contrast bolus administered to a subject after a first contrast bolus may be determined automatically based on the subject's individual contrast agent kinetics, such as based on an estimated arterial inflow function (AIF) curve and estimated venous outflow function (VOF) curve. The estimated AIF and VOF curves may be estimated based on a contrast curve (such as a tissue uptake curve) or segment of a contrast curve (e.g., an AIF signal) measured upon the prior first contrast agent injection (e.g., during a prior timing bolus or during a prior contrast scan). The contrast curve or segment of the contrast curve may comprise a measured contrast level in a region of interest (e.g., an artery, such as the internal carotid artery, or the brain) over a duration. The tissue uptake curve (TUC) or the AIF signal may be entered as input to a machine learning (ML) model that may output the estimated AIF curve and estimated VOF curve (and/or time points of interest from the AIF and VOF curves, such as arterial peak, venous peak, and venous return to baseline). Based on the output of the ML model, the desired time for administration of the second contrast bolus relative to the administration of the first contrast bolus may be determined, and then the second contrast bolus may be administered at the desired time. For example, the desired time may be the return to baseline of the VOF curve (the venous return to baseline, VRTB) for the first contrast bolus. The amount of time from an injection of contrast agent to the VRTB for the patient may be determined from the estimated AIF and VOF curves, and once this amount of time has elapsed since the administration of the first contrast bolus, the second contrast bolus may be administered. In this way, the precise amount of time for when to administer the second contrast bolus may be determined for each patient using information already available during a standard contrast scan protocol, thereby reducing the likelihood that the images reconstructed from scan data acquired during the second contrast scan will be non-diagnostic due to venous contrast agent contamination while preventing undue delays in commencing the second contrast scan that could otherwise negatively impact patient outcomes.

Figure 2:
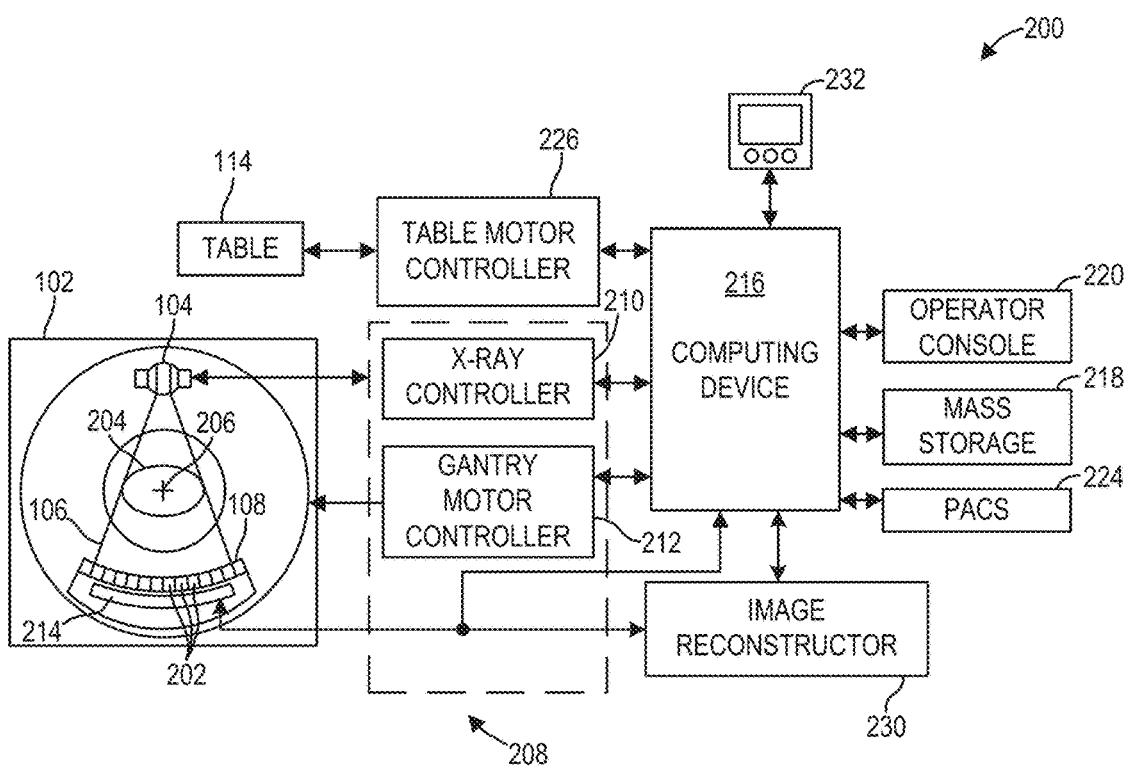
FIG. 2 shows a block schematic diagram of an exemplary imaging system, according to an embodiment.
Figure 3:
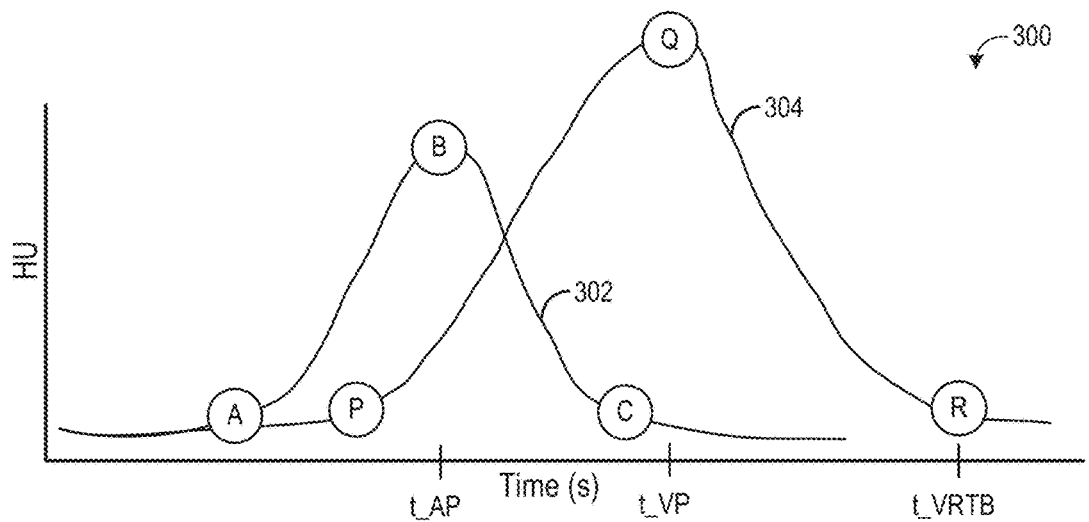
FIG. 3 shows a graph illustrating an example arterial inflow function (AIF) curve and an example a venous outflow function (VOF) curve generated during a contrast scan.
Figure 4:
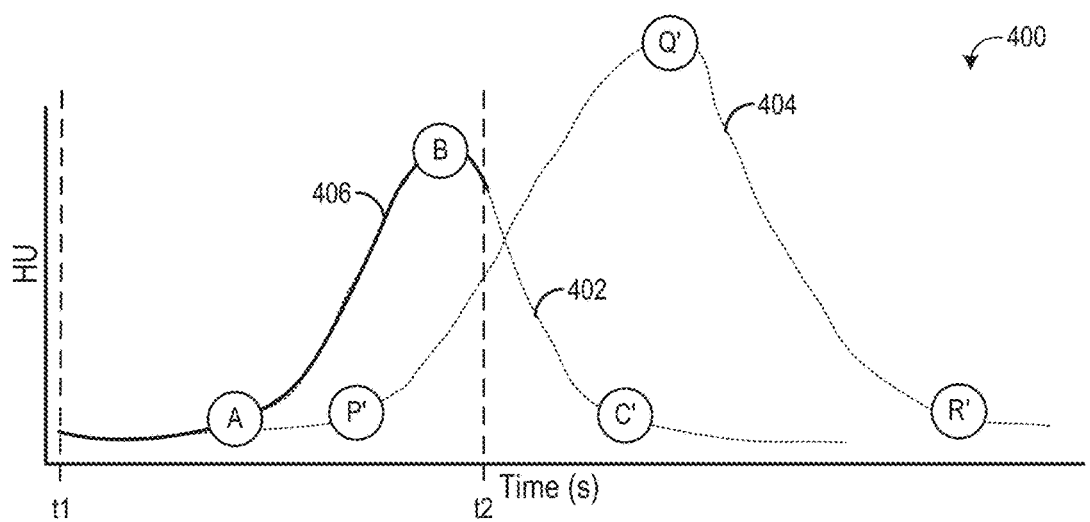
FIG. 4 shows a graph illustrating an estimated AIF curve and an estimated VOF curve generated according to an embodiment of the disclosure.
Figure 5:
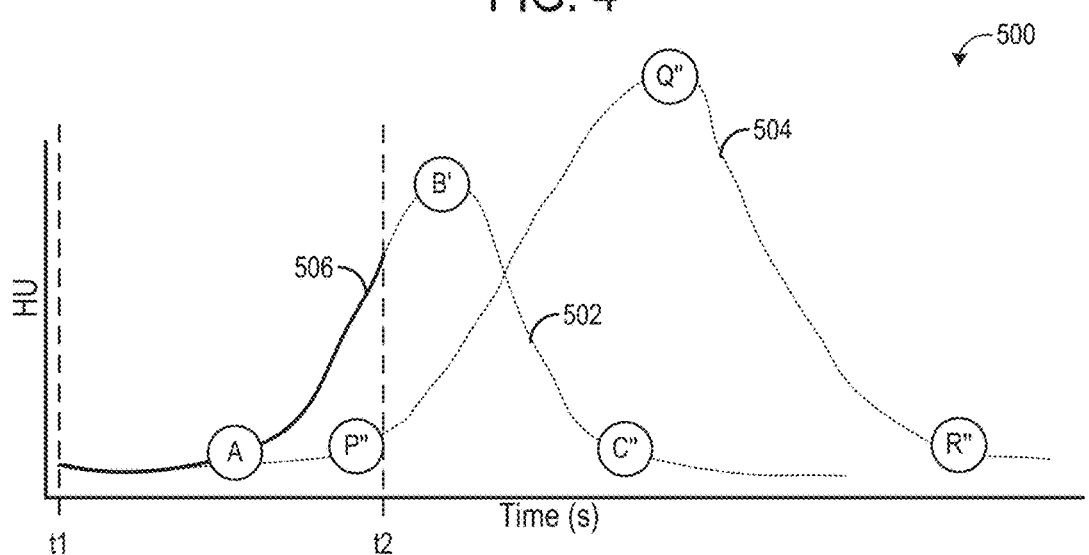
FIG. 5 shows a graph illustrating an estimated AIF curve and an estimated VOF curve generated according to another embodiment of the disclosure.
Figure 6:
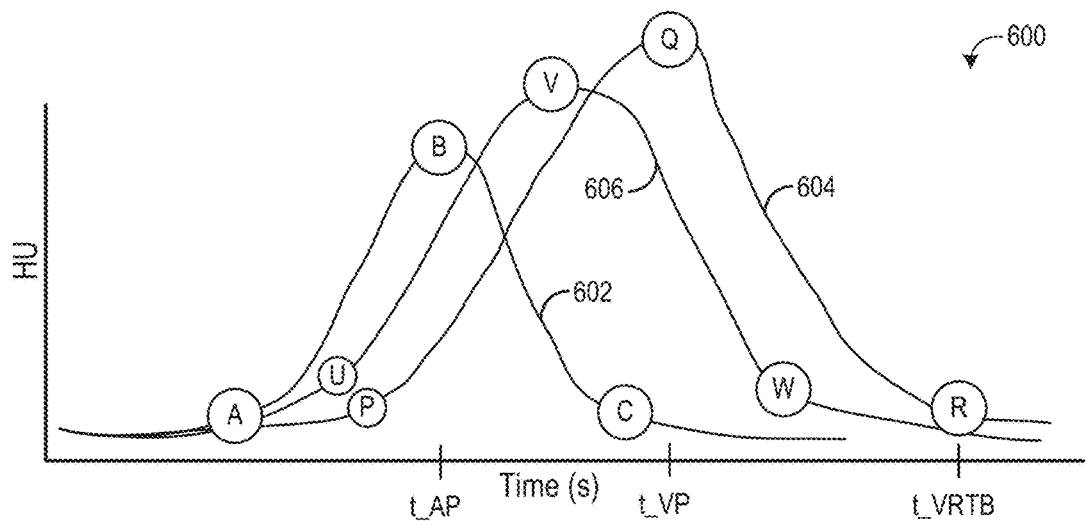
FIG. 6 shows a graph illustrating an example AIF curve, an example VOF curve, and an example tissue uptake curve (TUC) generated during a contrast scan.
Figure 7:
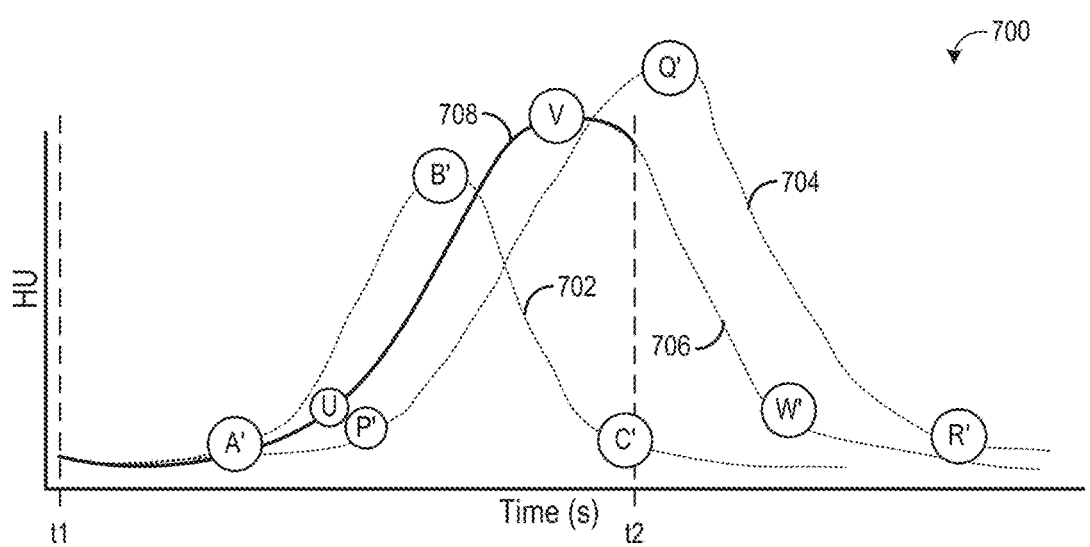
FIG. 7 shows a graph illustrating an estimated AIF curve, an estimated VOF curve, and an estimated TUC generated according to an embodiment of the disclosure.
Figure 8:
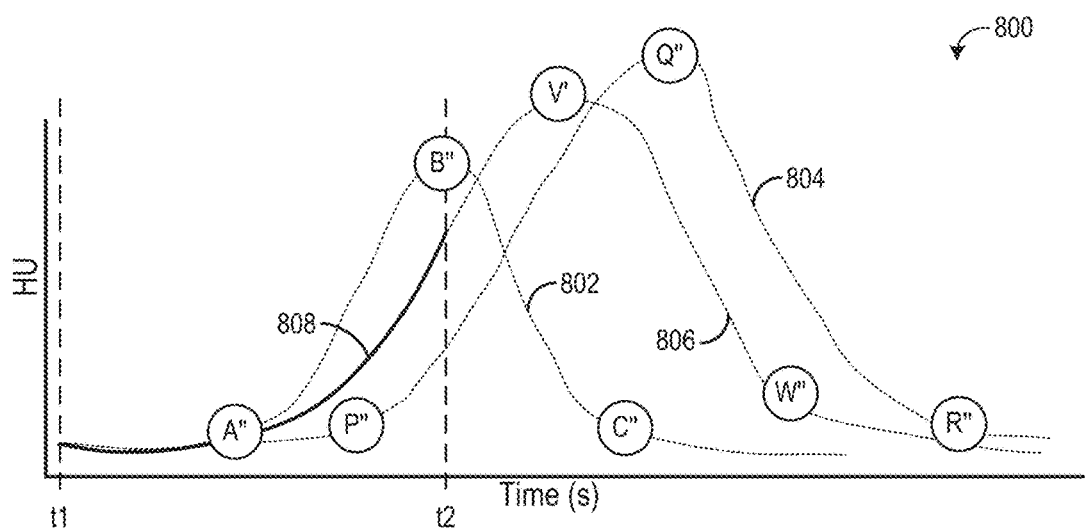
FIG. 8 shows a graph illustrating an estimated AIF curve, an estimated VOF curve, and an estimated TUC generated according to another embodiment of the disclosure.

An example of a computed tomography (CT) imaging system that may be used to perform the contrast scans in accordance with the present techniques is provided in FIGS. 1 and 2. As described above, the timing of the contrast scans may be dependent on the AIF and VOF curves of the contrast agent, which vary from patient to patient. FIG. 3 shows example AIF and VOF curves for a patient. A portion of the AIF curve may be directly measured prior to a first contrast scan commencing or during the first portion of the first contrast scan, and this portion may be used as input to a model to estimate the remaining AIF curve and the VOF curve for the patient, as shown in FIGS. 4 and 5. As another example, rather than measuring the AIF, tissue uptake of the contrast agent may be measured for a duration, and this measured portion of the tissue uptake curve (TUC) may be entered into a model to estimate the AIF and VOF curves. FIG. 6 shows example AIF, TUC, and VOF curves, while FIGS. 7 and 8 show example portions of the TUC that may be measured and used as input to estimate the AIF and VOF curves.

Figure 9A:
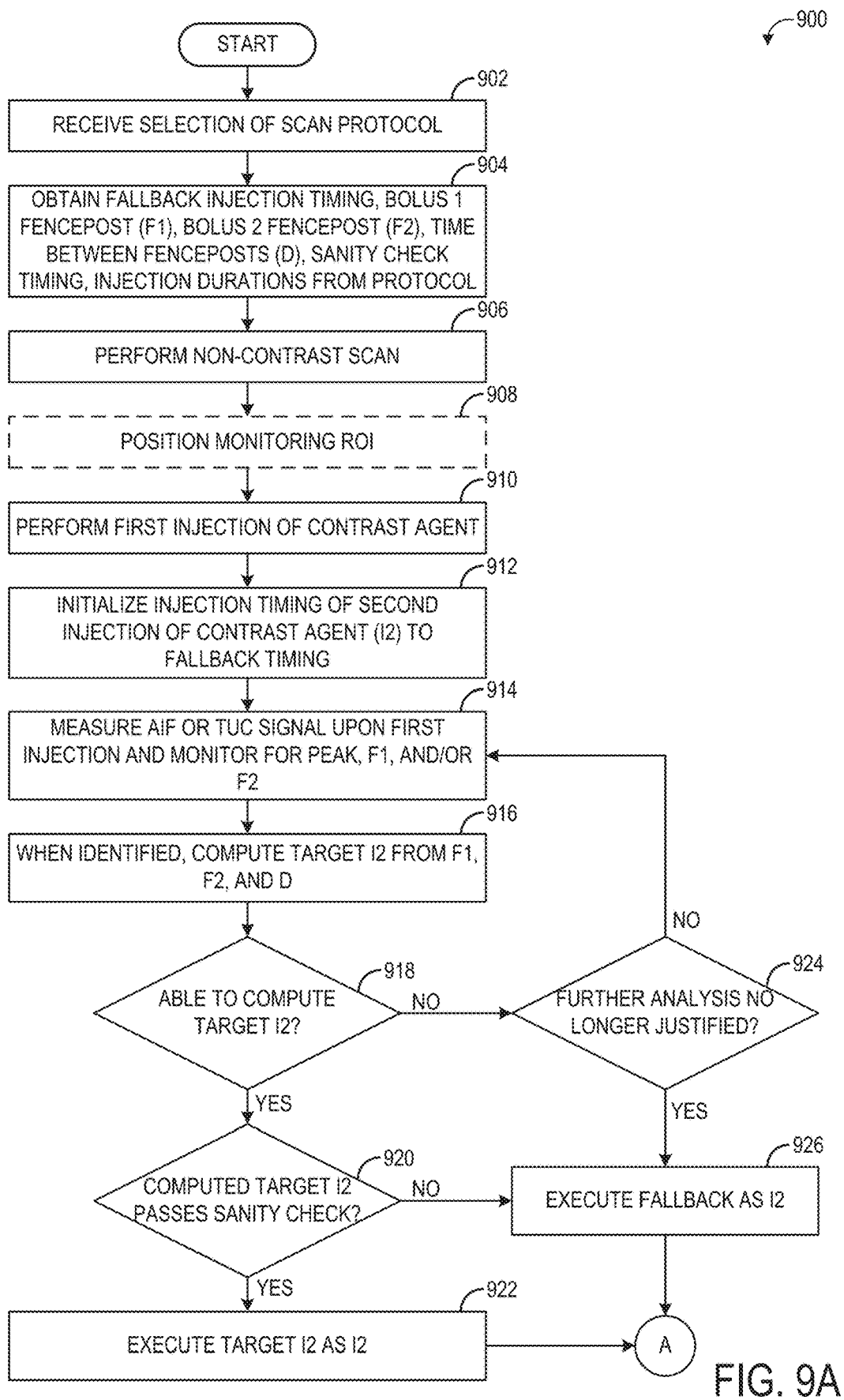
FIGS. 9A and 9B are a flow chart illustrating a method for performing a contrast scan with an adaptive contrast injection timing, according to an embodiment of the disclosure.
Figure 9B:
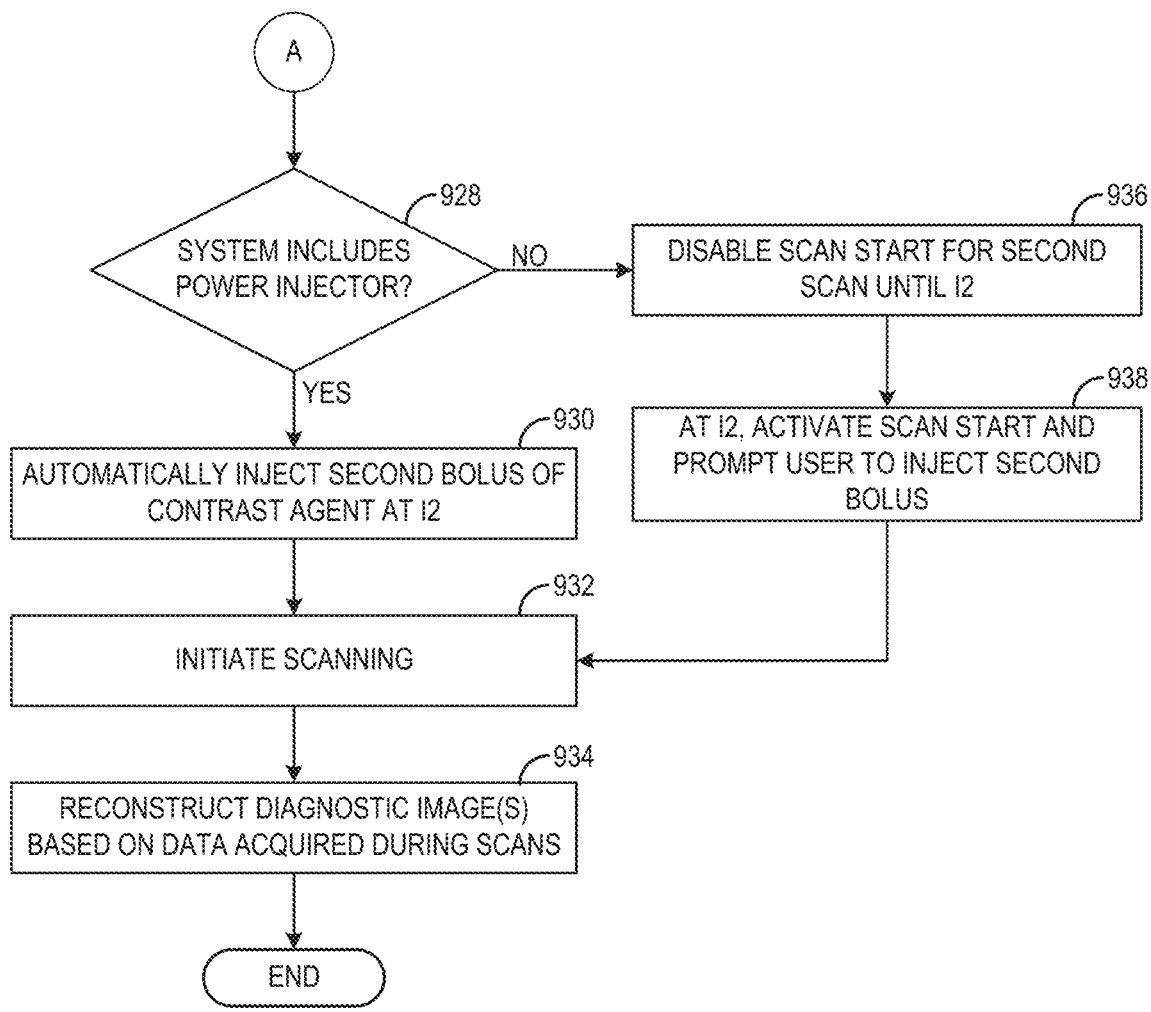
Figure 10A:
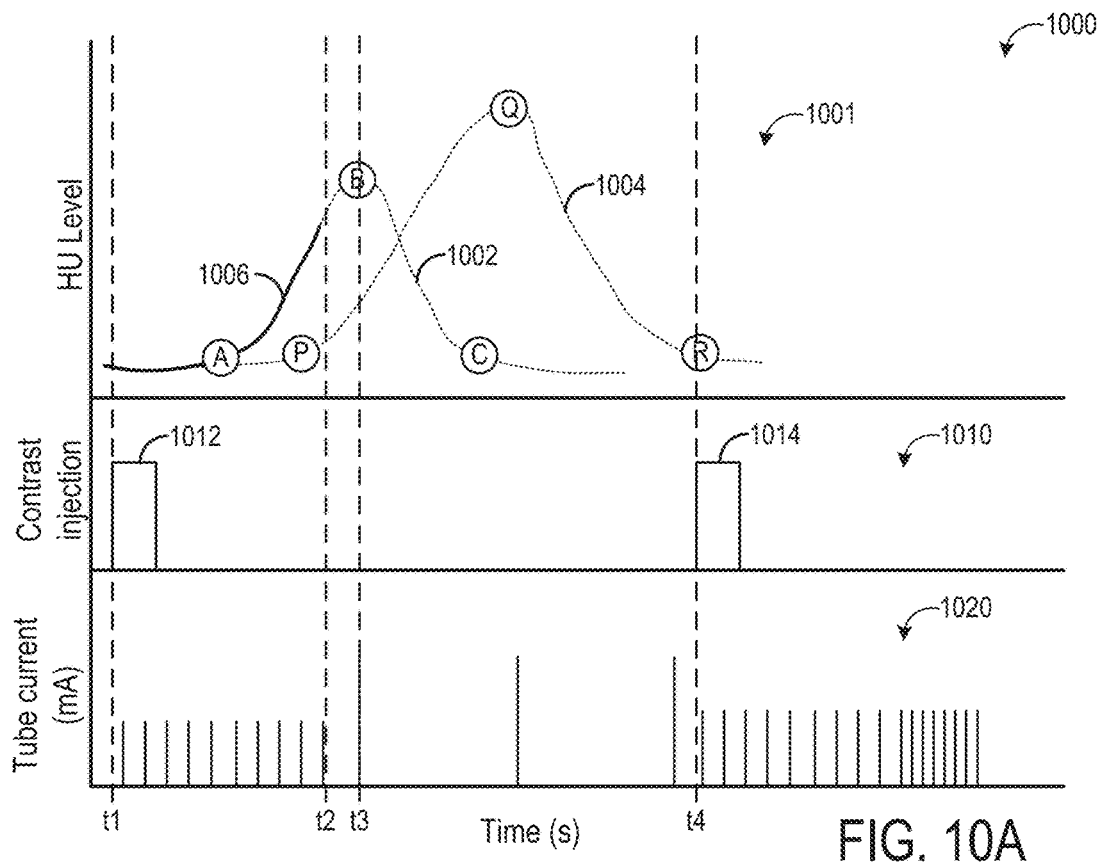
FIG. 10A is a first timeline illustrating monitored contrast level at a monitoring region of interest (ROI), contrast injection events, and imaging events across two contrast scans carried out according to the method of FIGS. 9A and 9B.
Figure 10B:
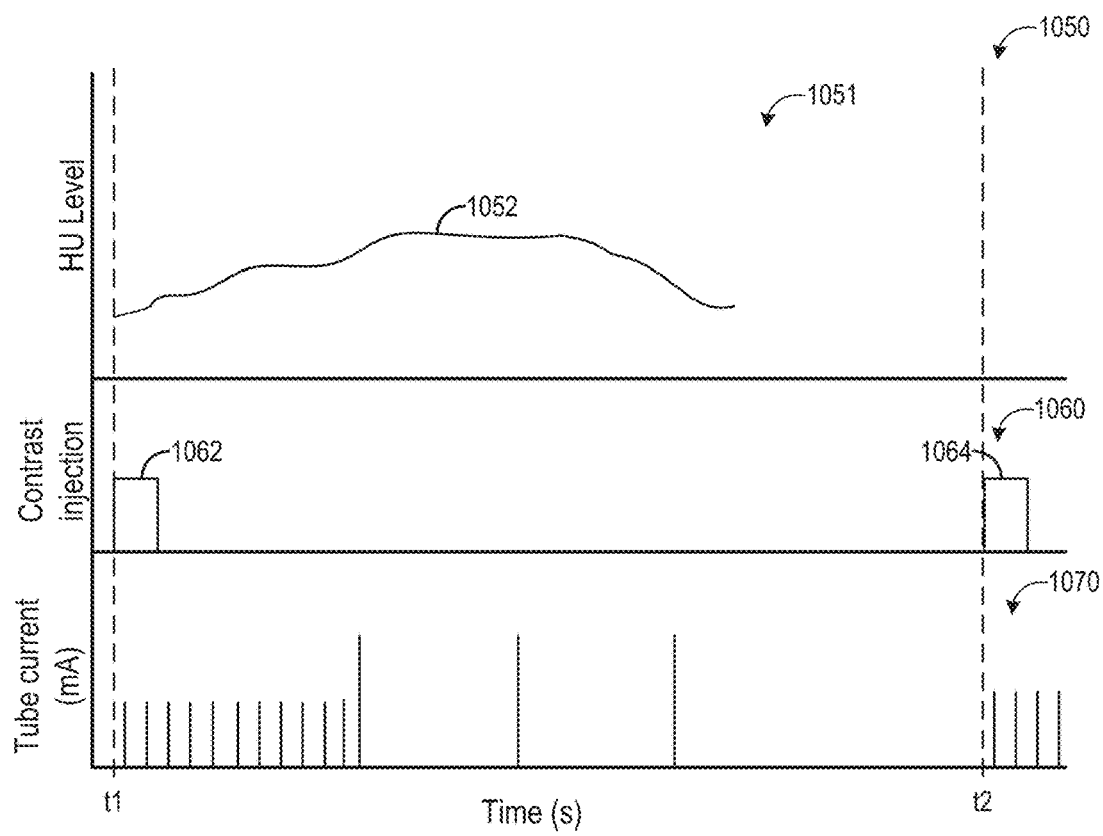
FIG. 10B is a second timeline illustrating monitored contrast level at a monitoring region of interest (ROI), contrast injection events, and imaging events across two contrast scans carried out according to the method of FIGS. 9A and 9B.

In this way, the timing of the administration of the second contrast bolus may be tailored to the individual patient by determining the injection timing of the second contrast bolus based on the contrast enhancement and washout kinetics of the first contrast bolus. For example, the contrast curves (e.g., the AIF and VOF curves) measured and/or estimated upon administration of the first contrast bolus may be monitored to identify a first fencepost of the first contrast bolus and predict a timing of a second fencepost of the second contrast bolus, and the second contrast bolus may be injected at a timing such that the first fencepost and the second fencepost are separated by a predefined amount of time. However, some patients may exhibit contrast curves that deviate from standard curves or are otherwise unusable for estimating the contrast curves or determining time points of interest (e.g., venous return to baseline) of the contrast curves. In such examples, scanning of those patients may be compromised as the system may not be able to determine when the second contrast bolus should be administered. To avoid delayed scanning, non-diagnostic images, or rescans in such patients, embodiments are disclosed herein where, while executing a contrast scan protocol that includes two contrast injections, the imaging system (e.g., CT system) is initialized to command (or prompt) injection of the second contrast bolus at a fallback timing that is independent of the individual contrast kinetics of the patient being scanned. The fallback timing may represent a worst-case scenario for timing of the second contrast injection that still ensures diagnostic images may be obtained for the scan following the second contrast injection. The system may monitor the contrast curve(s) generated/estimated from the first contrast bolus and if the curve(s) are sufficient for estimating/determining the fenceposts, an adaptive injection timing for the second contrast injection may be calculated and the second contrast injection may be performed at the adaptive injection timing. In doing so, diagnostic images may be ensured regardless of patient contrast kinetics, and for the majority of patients, the second contrast injection may be performed at a time optimized for that patient, which may be earlier than the fallback timing, thereby allowing the diagnostic images to be available earlier and hence avoiding patient health impacts caused by delayed image availability. A method for adaptive scan control including a fallback timing that may be superseded by an adaptive timing for the second contrast injection is shown in FIGS. 9A and 9B. FIGS. 10A and 10B show timelines of contrast injections, CT scan acquisitions, and example contrast curves for a first patient where adaptive timing is implemented and a second patient where the fallback timing is implemented, respectively. FIGS. 11A-11D show example adaptive injection timing profiles that may be applied to determine an adaptive timing for the second contrast injection.

Figure 12:
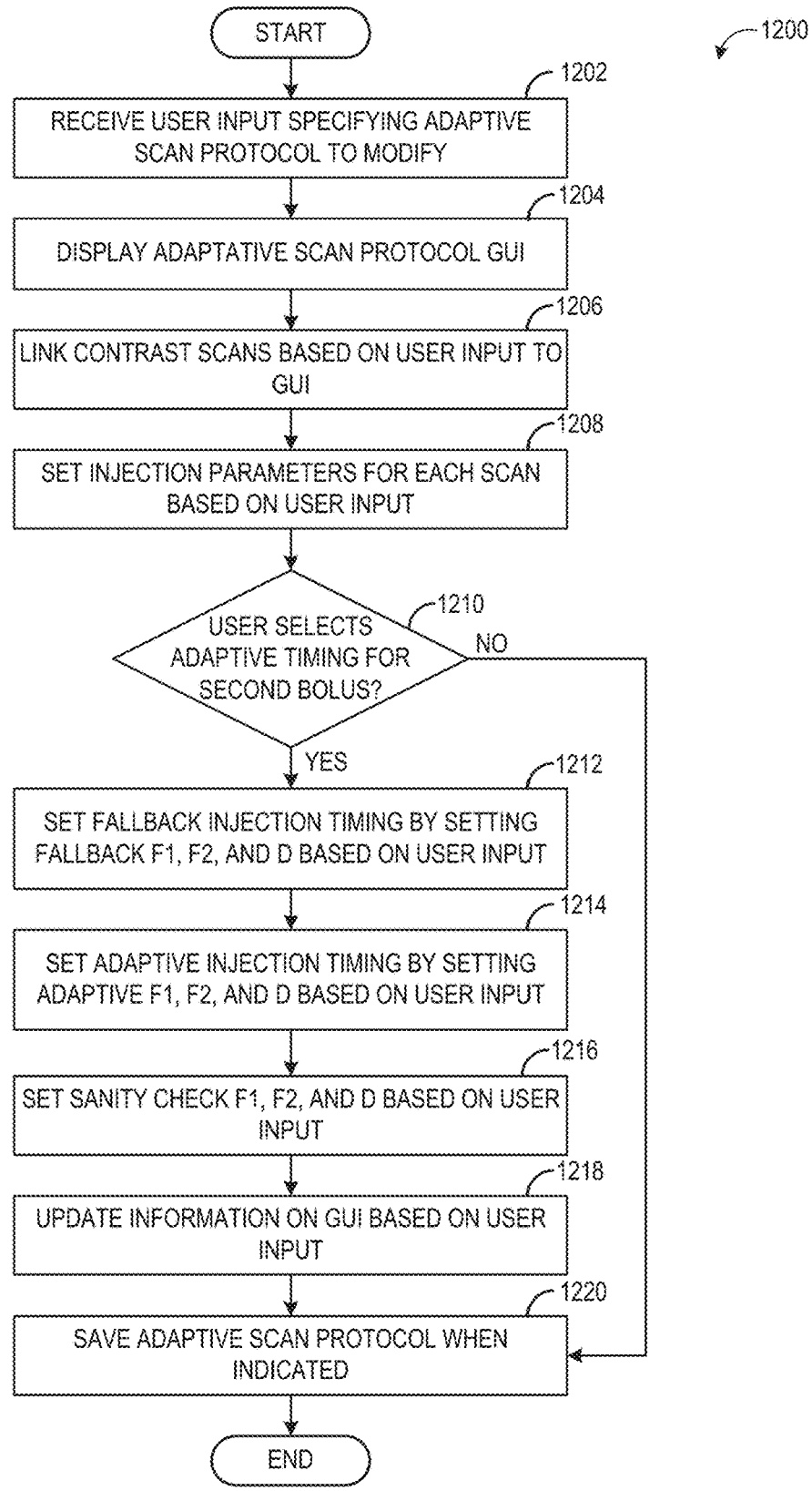
FIG. 12 is a flow chart illustrating a method for setting an adaptive contrast injection timing in advance via an adaptive scan protocol graphical user interface (GUI)
Figure 13:
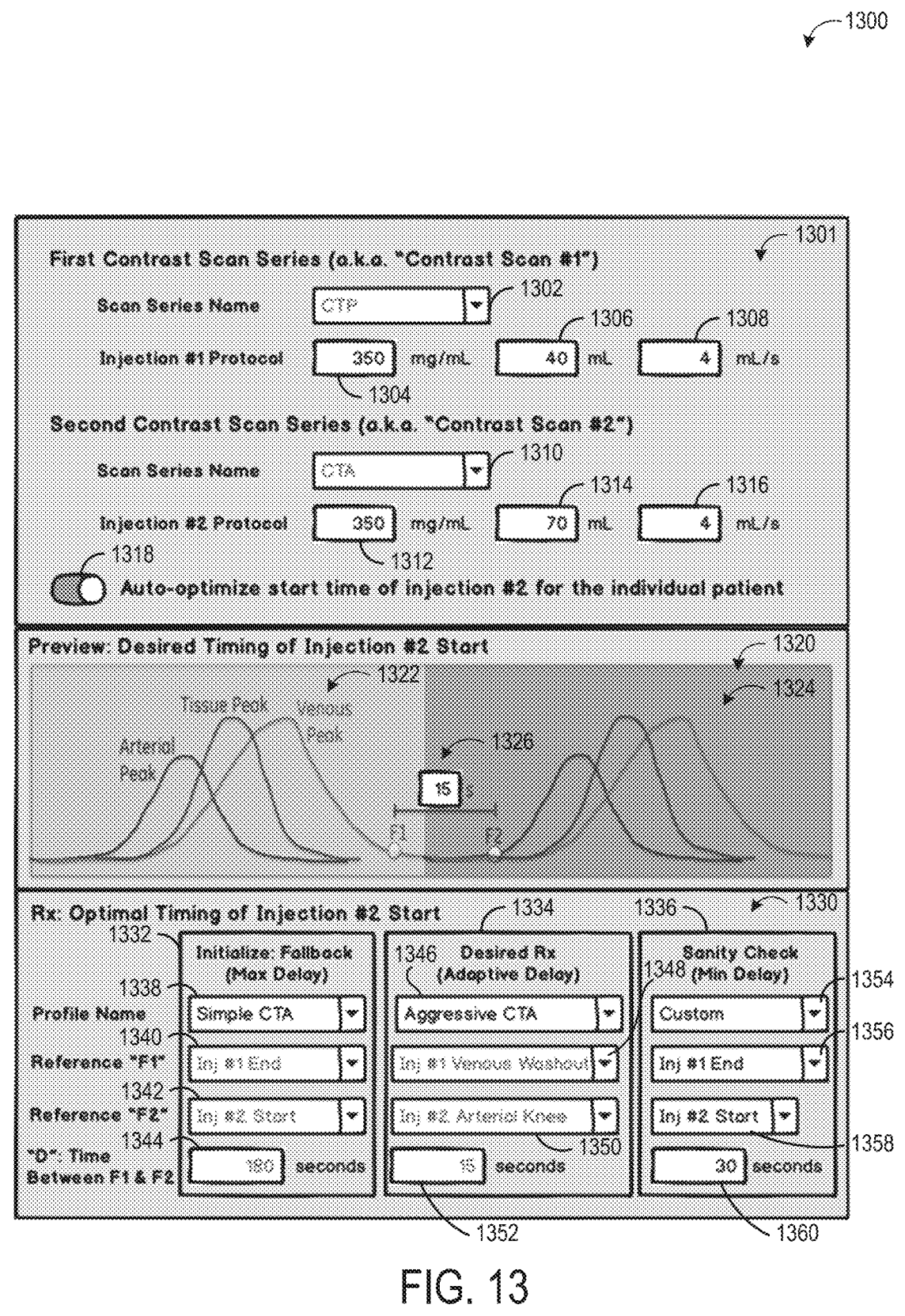
Figure 14:
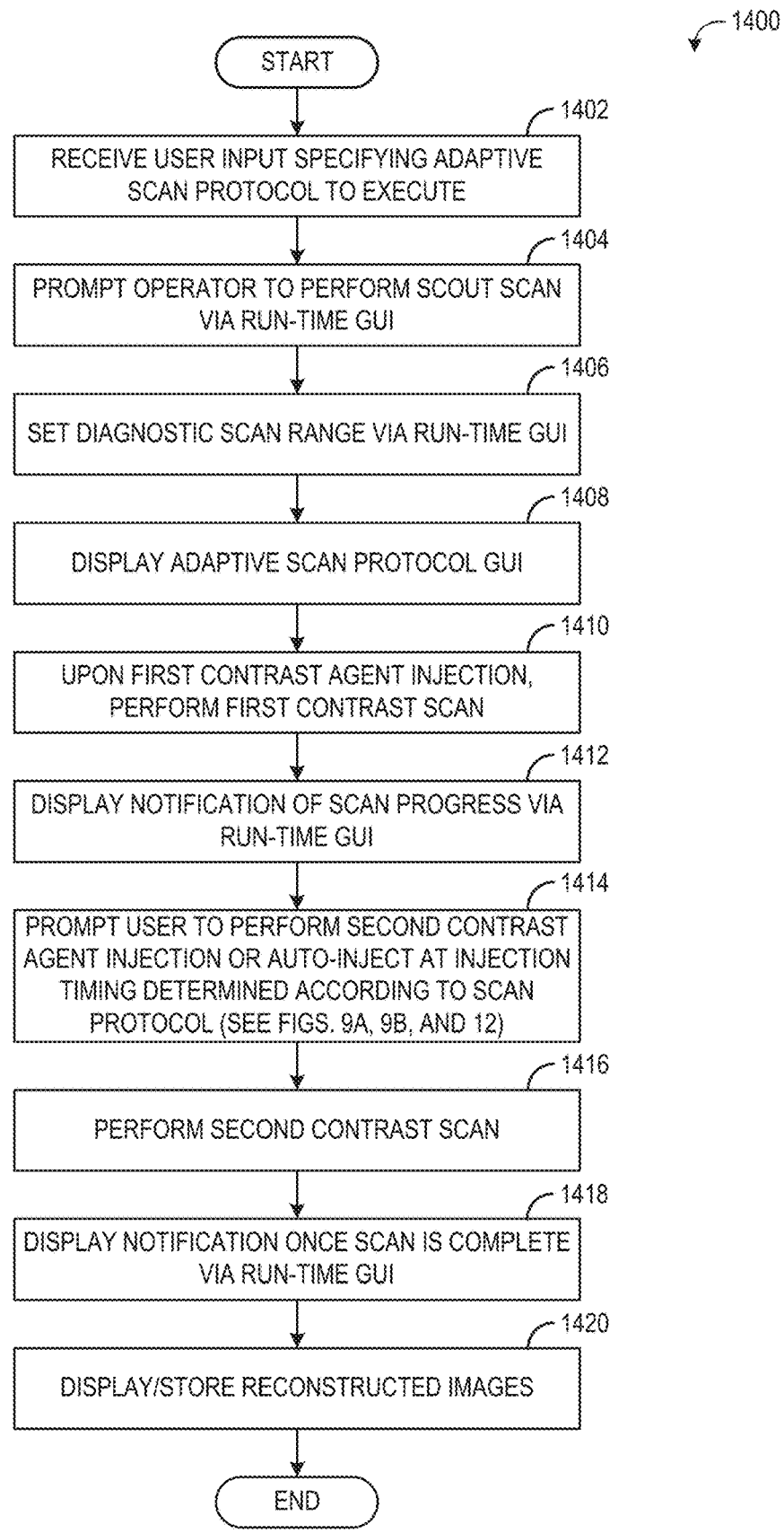
FIG. 14 is a flow chart illustrating a method for executing an adaptive contrast scan on a subject.
Figure 15:
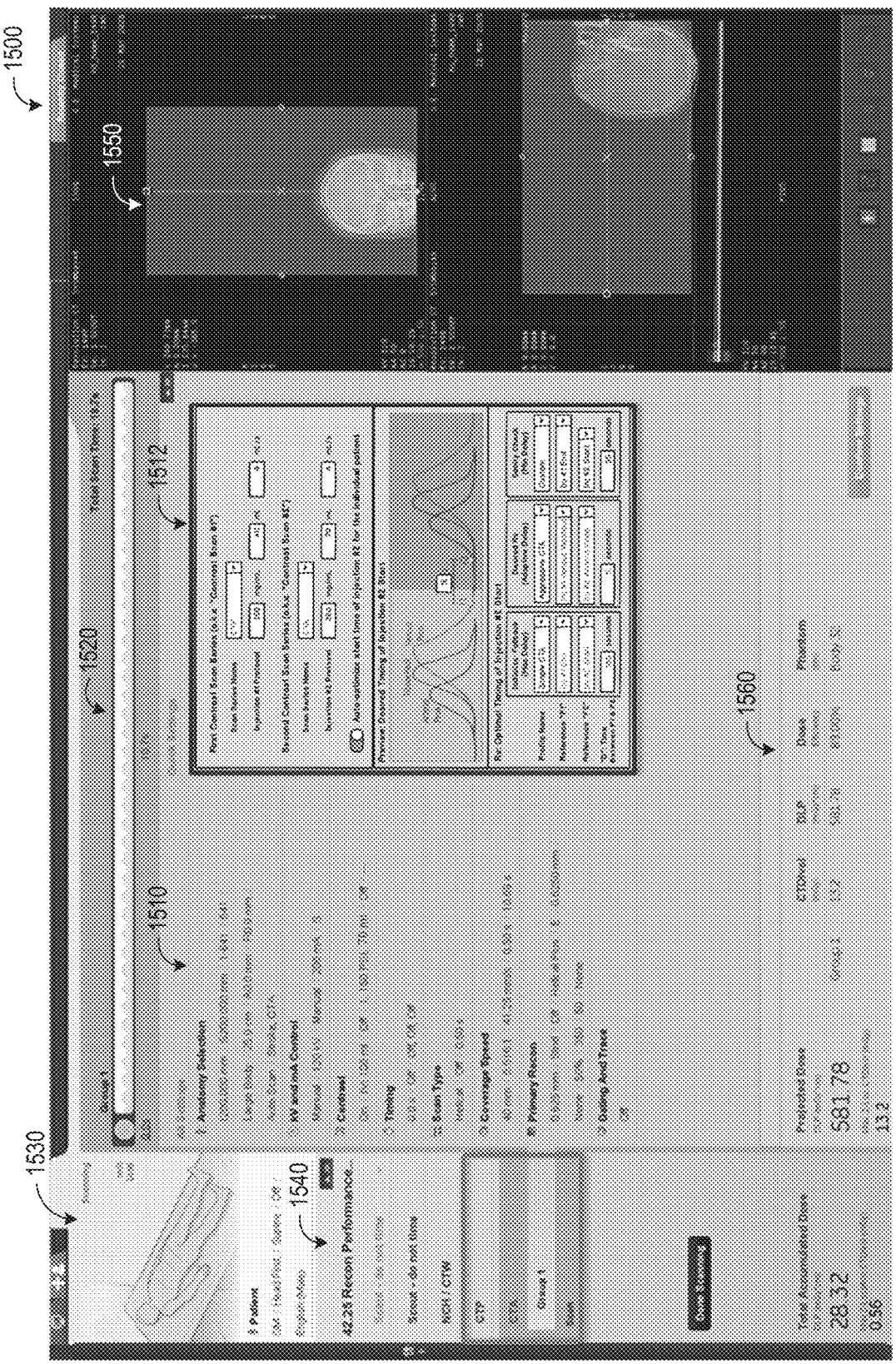
FIG. 15 shows an example of an adaptive scan run-time GUI.

Parameters of the fallback timing and the adaptive timing for the second contrast injection described above may be specified in advance according to an adaptive scan protocol defined by a lead technologist or other authorized user via input to an adaptive scan protocol graphical user interface (GUI). Then, during execution of the adaptive scan protocol by a scanning technologist or other imaging system operator, the fallback timing and adaptive timing parameters may be loaded and determined automatically, without requiring additional input from the scanning technologist. In doing so, the cognitive load placed on the scanning technologist at the time of scanning may be reduced, which may speed up the process of scanning the patient and reduce scanning errors. FIG. 12 shows a method for setting an adaptive scan protocol and FIG. 13 shows an example adaptive scan protocol GUI. FIG. 14 shows a method for executing an adaptive scan protocol, which may include user interaction with a run-time GUI, an example of which is shown in FIG. 15.

Though a CT system is described by way of example, it should be understood that the present techniques may also be useful when applied to images acquired using other imaging modalities, such as tomosynthesis, MRI, C-arm angiography, and so forth. The present discussion of a CT imaging modality is provided merely as an example of one suitable imaging modality. Further, while the present techniques may be discussed herein with respect to head/neck scans such as acute stroke scan protocols, the present techniques may be applied during other contrast scan protocols, such as cardiac scans.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 (see FIG. 2) for use in imaging the subject 112 laying on a table 114. Specifically, the x-ray source 104 is configured to project the x-ray radiation beams 106 towards a detector array 108 positioned on the opposite side of the gantry 102. Although FIG. 1 depicts only a single x-ray source 104, in certain embodiments, multiple x-ray sources and detectors may be employed to project a plurality of x-ray radiation beams for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of an x-ray radiation beam by the object. Each detector element of the array produces a separate electrical signal that is a measurement of the x-ray beam attenuation at the detector location. The attenuation measurements from all the detector elements are acquired separately to produce a transmission profile.

In some CT systems, the x-ray source and the detector array are rotated with a gantry within the imaging plane and around the object to be imaged such that an angle at which the x-ray beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202.

Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes (such as the method described below with reference to FIGS. 9A and 9B) described further herein may be stored as executable instructions in non-transitory memory on a computing device (or controller) in imaging system 200. In an embodiment, computing device 216 may include the instructions in non-transitory memory, and may apply the methods described herein, at least in part, set contrast scan protocols, to measure AIF or TUC signals from a plurality of reconstructed images after receiving the reconstructed images from image reconstructor 230, and adapt scan prescriptions on the fly based on the measured AIF or TUC signals. In other embodiments, image reconstructor 230 may include such executable instructions in non-transitory memory, and may apply the methods described herein to adaptively plan and control contrast scans. In yet another embodiment, the methods and processes described herein may be distributed across image reconstructor 230 and computing device 216.

In one embodiment, the display 232 allows the operator to evaluate the imaged anatomy, view measured and/or estimated AIF and VOF curves, trigger aspects of the contrast scans, set scan protocols, and the like. The display 232 may also allow the operator to select a region of interest (ROI) and/or request patient information, for example, via a graphical user interface (GUI) for a subsequent scan or processing.

FIG. 3 shows a graph 300 depicting an example AIF curve 302 and an example VOF curve 304 each plotted as HU as a function of time. AIF curve 302 represents the change in the arterial inflow of a contrast agent over time for a patient, and VOF curve 304 represents the change in the venous outflow of the contrast agent over time for the patient. The AIF curve 302 may be measured at an arterial ROI, such as anterior cerebral artery or internal carotid artery, and may include a measurement of signal intensity in the arterial ROI relative to a baseline intensity (e.g., in the arterial ROI prior to contrast injection). The VOF curve 304 may be measured at a venous ROI, such as the superior sagittal sinus, and may include a measurement of the signal intensity in the venous ROI relative to a baseline intensity (e.g., in the venous ROI prior to contrast injection).

The AIF curve 302 may include an arterial ascent knee at approximately point A on the curve, an arterial peak at point B on the curve, and an arterial decent knee at approximately point C on the curve. The amount of time from contrast injection until the arterial peak is reached may be the time to arterial peak, indicated as t_AP on FIG. 3. The VOF curve 304 may include a venous ascent knee at approximately point P on the curve, a venous peak at point Q on the curve, and a venous decent knee at approximately point R on the curve. The amount of time from contrast injection until the venous peak is reached may be the time to venous peak, indicated as t_VP on FIG. 3. The amount of time from contrast injection until the venous return to baseline (VRTB) is reached may be the time to VRTB, indicated as t_VRTB on FIG. 3.

The amount of time it may take to reach the points marked on the curves in FIG. 3 may vary from patient to patient, as body weight, cardiac function, and other factors may impact the contrast agent inflow and outflow rate. As will be explained in more detail below, certain contrast scan protocols, such as perfusion and angiography scans, rely on the AIF and/or VOF curves, and the timing of one or more of the points described above (e.g., the arterial peak) may be determined and used as a trigger for commencing diagnostic imaging, adjusting scan parameters, and the like. However, some scan protocols are condensed as much as possible so that diagnostic information may learned as quickly as possible in order to facilitate patient care. For example, scan protocols carried out as part of an acute stroke assessment may be designed to be as short as possible, while still collecting the needed diagnostic image information, so that needed patient care may be administered as quickly as possible. Thus, the amount of time needed to completely measure both the AIF curve and the VOF curve for a patient prior to initiation of the diagnostic scan(s) may delay patient care and negatively impact patient outcomes. Further, when the imaging system includes x-rays directed to the patient (such as the CT system described above with respect to FIGS. 1-2), it may be desired to minimize patient radiation exposure. Thus, acute stroke and other contrast scan protocols may include a short measurement of the AIF curve, for example, and scan protocol adjustments may be based on this limited information and/or certain aspects of the scan protocols may be carried out with fixed timing that is not changed from patient to patient. While such protocols may be suitable for ensuring that most scans generate sufficient diagnostic information, some scans may result in images that are not suitable for diagnosing the patient condition or may lead to unnecessary radiation exposure.

Thus, prior to or during the beginning of a contrast scan, a small segment of the AIF curve may be measured and this AIF curve measurement (referred to as an AIF signal) may be used to estimate the remainder of the AIF curve as well as the VOF curve. To ensure an accurate estimation, a machine learning model may be deployed that is trained using a plurality of different AIF signals measured from different patients along with associated full AIF and VOF curves (or associated points of interest on the AIF and VOF curves, such as the points labeled on FIG. 3 and described above). The measured AIF signal may be entered into the trained and validated machine learning model, and the model may output an estimated AIF curve and estimated VOF curve, or the model may output the time to one or more significant points of the AIF and VOF curves, such as the time to arterial peak, the time to venous peak, and the time to venous return to baseline. The scan protocols may then be adapted on the fly on a patient by patient basis using the estimated AIF and VOF curves and/or estimated time points of the AIF and VOF curves.

FIG. 4 shows a graph 400 depicting an estimated AIF curve 402 and estimated VOF curve 404 each estimated according to a first estimation method, referred to as an augmented timing bolus (aTB) estimation. A timing bolus may include a small amount of contrast agent that is administered before a contrast scan is initiated. The inflow of the contrast agent of the timing bolus may be monitored and used to set parameters for the follow-on contrast scan. As shown, a first segment 406 of the AIF curve is measured as described above (e.g., in a ROI based on change in HU level relative to a baseline level). The first segment 406 may commence when the timing bolus is administered (e.g., at time t1 in FIG. 4) and end after the arterial peak (e.g., at time t2 in FIG. 4). The first segment 406 may be entered into a model to estimate the remaining portion of the estimated AIF curve 402 and all of the estimated VOF curve 404. As a result, time points A and B are measured while time points V, C', Q', and R' are estimated. In some examples, the first segment 406 may extend beyond what is shown in FIG. 4. For example, rather than terminating the measurement of the AIF curve at time t2, the measurement may extend until another suitable, later time. As the first segment is lengthened, the accuracy of the estimation of the subsequent time points may be increased, but extending the measurement period may increase the radiation dosage to the patient.

FIG. 5 shows a graph 500 depicting an estimated AIF curve 502 and estimated VOF curve 504 each estimated according to a second estimation method, referred to as an augmented smart prep (aSP) estimation. Smart prep may refer to an in-flight AIF measurement that occurs using the same contrast agent bolus that is administered for the contrast scan. The inflow of the contrast agent of the contrast scan bolus may be monitored and used to set parameters for the in-flight contrast scan. As shown, a first segment 506 of the AIF curve is measured (as described above). The first segment 506 may commence when the contrast bolus is administered (e.g., at time t1 in FIG. 5) and end before the arterial peak (e.g., at time t2 in FIG. 5), while arterial contrast enhancement is still increasing. The first segment 506 may be entered into a model to estimate the remaining portion of the estimated AIF curve 502 and all of the estimated VOF curve 504. As a result, time point A is measured while time points B', P'', C'', Q'', and R'' are estimated. Time points P'', C'', and R'' are given a double prime notation to indicate that the estimation of these time points may not be as accurate as the estimation of those time points using the aTB estimation method, given that the aSP estimation relies on less measured data than the aTB estimation.

Thus, the AIF and VOF curves (or selected time points of the AIF and VOF curves) may be estimated using a relatively short measured segment of the AIF curve that is entered into a machine learning model. The aTB estimation method, described with respect to FIG. 4, may result in a more accurate estimation of the AIF and VOF curves than the aSP estimation method, given the additional measured data that may be entered into the model. However, the aTB estimation method relies on a timing bolus or other separate contrast agent injection, and thus may be more time-consuming than the aSP estimation method.

While the aTB and aSP estimation methods were both described as being based on a single arterial ROI, it is to be understood that multiple arterial ROIs could be measured and combined (e.g., averaged) to measure the AIF curve. Further, the VOF curve could be measured for the same time period as the AIF curve (e.g., from time t1 until the respective time t2) by monitoring a venous ROI, and the measured segment of the VOF curve could be used as input to the model in addition to the measured segment of the AIF curve, which may result in a more robust estimation of the remaining portions of the AIF and VOF curves.

The arterial ROI and venous ROI described above may be positioned at any suitable location where arterial inflow and venous outflow, respectively, of contrast agent may be detectable, and the selection of where to position the arterial ROI and/or venous ROI may depend on the scan protocol (e.g., what anatomy is going to be imaged in the contrast scan). However, some anatomy, such as the brain, may present challenges for arterial or venous ROI placement, as the ability to visualize certain anatomical features may require presence of a contrast agent. Thus, to place an arterial or venous ROI in the head/brain, a separate administration of contrast agent may be needed to even place the ROI, which may make arterial or venous ROI placement in the head unpractical. Thus, the arterial ROI and/or venous ROI may typically be placed in the neck area or another adjacent anatomy, and then the patient may be moved relative to the CT imaging system (e.g., via table movement) to position the head in the proper location for the contrast scan. However, this additional table movement may prolong the duration of the scan session and/or make some adaptive scan protocols unpractical. Thus, as will be explained below, another method for estimating the AIF and VOF curves for use in adaptive scan protocols includes monitoring tissue uptake of contrast agent over an entire view/image rather than a small ROI.

FIG. 6 shows a graph 600 depicting an example AIF curve 602, an example VOF curve 604, and an example tissue uptake curve (TUC) 606 each plotted as HU as a function of time. AIF curve 602 and VOF curve 604 may be the same as AIF curve 302 and VOF curve 304 described above with respect to FIG. 3. TUC 606 may represent the change in detected contrast agent in a tissue of interest, as the contrast agent is taken up by the tissue and then depleted from the tissue. To measure the TUC, tissue of interest (e.g., the brain parenchyma) may be segmented in each of a plurality of reconstructed images, and the overall or average HU of in the segmented region of each of the plurality of reconstructed images may be determined relative to a baseline level and plotted over time. Additional details regarding the tissue segmentation and TUC signal measurement are provided below with respect to FIG. 16.

The AIF curve 602 may include the time points discussed above (e.g., A, B, and C) and the VOF curve 604 may include the time points discussed above (e.g., P, Q, and R). TUC 606 may include an ascent knee at approximately point U on the curve, a TUC peak at point V on the curve, and a decent knee at approximately point W on the curve. The timing of significant points are shown in FIG. 6, including t_AP, t_VP, and t_VRTB.

A segment of the TUC may be measured and then entered into a model to predict the AIF curve and the VOF curve, the remainder of the TUC, and/or time points of interest, similar to the aTB and aSP estimation methods described above. FIG. 7 shows a graph 700 depicting an estimated AIF curve 702, an estimated VOF curve 704, and an estimated TUC 706, each estimated according to a first TUC estimation method. The tissue uptake of a contrast agent (e.g., of a timing bolus) may be monitored and used to set parameters for the follow-on contrast scan. As shown, a first segment 708 of the TUC is measured as described above (e.g., a change in HU level relative to a baseline level measured across a plurality of images). The first segment 708 may commence when the timing bolus is administered (e.g., at time t1 in FIG. 7) and end after the TUC peak (e.g., at time t2 in FIG. 7). The first segment 708 may be entered into a model to estimate the remaining portion of the estimated TUC 706 and all of the estimated AIF curve 702 and VOF curve 704. As a result, time points U and V are measured while time points A', B', C', V, Q', and R' are estimated.

FIG. 8 shows a graph 800 depicting an estimated AIF curve 802, an estimated VOF curve 804, and an estimated TUC 806 each estimated according to a second TUC estimation method. The second TUC estimation method may be performed in-flight with a contrast scan, using the same contrast agent bolus that is administered for the contrast scan. The tissue uptake of the contrast agent may be monitored and used to set parameters for the in-flight contrast scan. As shown, a first segment 808 of the TUC curve is measured (as described above). The first segment 808 may commence when the contrast bolus is administered (e.g., at time t1 in FIG. 8) and end before the TUC peak (e.g., at time t2 in FIG. 8), while tissue uptake of the contrast agent is still increasing. The first segment 808 may be entered into a model to estimate the remaining portion of the TUC 806 and all of the estimated AIF curve 802 and all of the estimated VOF curve 804. As a result, time point U is measured while time points A", B", V', W", P", C", Q", and R" are estimated. Time points with a double prime notation indicate that the estimation of these time points may not be as accurate as the estimation of those time points using the first TUC estimation method, given that the second TUC estimation relies on less measured data than the first TUC estimation.

Thus, the AIF, TUC, and VOF curves (or selected time points of the AIF, TUC, and VOF curves) may be estimated using a relatively short measured segment of the TUC that is entered into a machine learning model. The first TUC estimation method, described with respect to FIG. 7, may result in a more accurate estimation of the AIF and VOF curves than the second TUC estimation method described with respect to FIG. 8, given the additional measured data that may be entered into the model. However, the first TUC estimation method may rely on a timing bolus or other separate contrast agent injection, and thus may be more time-consuming than the second TUC estimation method.

As will be explained in more detail below, contrast curves (e.g., an AIF curve, an VOF curve, and/or a TUC) of a patient measured and/or estimated upon administration of a first contrast bolus may be used to determine an optimal time to administer a second contrast bolus for the patient. Depending on the scan protocol, the first contrast bolus may be the contrast bolus for a first contrast scan, and thus the second contrast bolus may be the contrast bolus for a second contrast scan following the first contrast scan, though other examples are possible, such as the first contrast bolus being a timing bolus. To ensure all patients are scanned even if the measured and/or estimated contrast curves are not usable to determine an optimal injection timing for the second contrast bolus, the scan protocol may include a fallback, default timing for the second contrast injection, as explained below.

FIGS. 9A and 9B show a flow chart illustrating a method 900 for timing a second contrast agent injection (e.g., second bolus of contrast agent) based on patient-specific contrast agent timing parameters determined from a first contrast agent injection. Method 900 is described with respect to the system and components described above with respect to FIGS. 1-2 but could be carried out with other systems/components without departing from the scope of this disclosure. Method 900 may be carried out according to instructions stored in non-transitory memory of a computing device (e.g., computing device 216 of FIG. 2). Method 900 may include a determination of a target timing for initiating injection of a contrast agent for a second contrast scan following a first contrast scan, or otherwise determining the target timing of a contrast agent injection where contrast agent contamination from a prior injection of contrast agent (e.g., a timing bolus) may confound accurate diagnosis of a patient condition. Thus, method 900 may be performed in response to user selection of a scanning protocol that includes two contrast scans performed in rapid succession, such as a CTA followed by a CTP or a CTP followed by a CTA, or in response to user selection of a scanning protocol that includes a timing bolus of contrast agent followed by a contrast scan, such as a CTP.

At 902, a selection of a scan protocol is received. The scan protocol may dictate the type of scan(s) to be carried out, such as a CTP followed by a CTA, the target anatomical feature(s) to be imaged and/or a diagnostic goal of the scan(s) (e.g., a head scan to diagnose ischemic stroke) as well as the scan prescription for each scan, such as the x-ray tube current and voltage, slice thickness, acquisition rate, and so forth. The scan protocols may be stored in a protocol library and may be set by a lead technologist or other authorized user, as will be explained in more detail below with respect to FIG. 12. In scan protocols where two scans are carried out, such as a CTA following a CTP or vice versa, the scan protocol may include an indication of when the second contrast bolus is to be injected relative to the first contrast bolus. In some examples, the scan protocol may include a set profile that dictates when the second contrast bolus is to be injected relative to injection of the first contrast bolus. Example profiles may include "conservative," "aggressive," "super aggressive," and "simple neuro." More detail on these protocols is presented below with respect to FIGS. 11A-11D.

At 904, a fallback injection timing, fencepost 1 (F1) of the first bolus, fencepost (F2) of the second bolus, time/delay between fenceposts (D), sanity check timing, and injection durations are obtained from the selected scan protocol. The fencepost F1 may be a marker of the first contrast bolus (administered for the first contrast scan of the scan protocol or the timing bolus), such as venous washout time (R1, also referred to as venous return to baseline or VRTB) for the first contrast bolus, arterial washout time C1 for the first contrast bolus, a first injection start time I1 for the first contrast bolus, or injection end time E1 for the first contrast bolus. The fencepost F2 may be a marker of the second contrast bolus (administered for the second contrast scan of the scan protocol), such as arterial enhancement start time A2 for the second contrast bolus or a second injection start time I2 for the second contrast bolus. D is the minimum time in between F1 and F2 in seconds. Additionally, the sanity check may be defined as a minimum rational time between E1 (bolus 1 injection end) and I2 (the second injection start). The sanity check time (e.g. SanCh_postE1) may be 60 seconds or another suitable amount of time. The injection durations may be the amount of time of each contrast bolus injection.

As will be explained in more detail below, the start time of the injection of the second contrast bolus (I2) may be determined from F1, F2, and D. Since each fencepost F1 and F2 is a marker for the two contrast boluses, and D is the minimum time between the two fenceposts, I2 may thus be determined by estimating/measuring when F1 occurs and/or when F2 is predicted to occur by monitoring the contrast enhancement of the first contrast injection, and then setting the injection timing of the second contrast injection so that F2 occurs D seconds after F1.

In one example, if the scan protocol includes a "conservative" profile, then F1 may be set to R1, F2 may be set to the second injection start time I2, and D may be set to 2 seconds. In this scenario, I2 will be calculated as the sum of R1 and D, such that the second contrast bolus will be administered 2 seconds after venous return to baseline of the first contrast bolus. The intent is to actuate the second injection I2 at bolus 1 venous washout (R1) plus a fixed delay (D).

In another example, if the scan protocol includes an "aggressive" profile, then F1 may be set to R1, F2 may be set to A2, and D may be set to 6 seconds. In this scenario, I2 may be calculated as the sum of R1 and D minus A1, as the protocol will assume that A2 is equal to A1. The intent of this profile is to actuate I2 such that bolus 2 arterial enhancement start (A2) occurs at bolus 1 venous washout (R1) plus a fixed delay (D).

In another example, if the scan protocol includes a "super aggressive" profile, then F1 may be set to C1, F2 may be set to the arterial enhancement start time A2, and D may be set to 8 seconds. In this scenario, I2 may be calculated as the sum of C1 and D minus A1, as the protocol will assume that A2 is equal to A1 and thus this statement is equivalent to the sum of C1 and D minus A1. The intent of this profile to actuate I2 such that bolus 2 arterial enhancement start (A2) occurs at bolus 1 arterial washout C1 plus a fixed delay (D).

In another example, if the scan protocol includes a "simple neuro" profile, then F1 may be set to E1, the first injection end time. F2 may be set to the second injection start time I2, and D may be set to 110 seconds. In this scenario, I2 will be calculated as the sum of E1 and D. Other profiles are possible, and the profiles presented above are exemplary and non-limiting.

At 906, a non-contrast scan is optionally performed. The non-contrast scan may be taken to establish a baseline image for the area to be monitored before delivery of a contrast agent. The baseline image may then be used to align the patient and the region of interest within the imaging device.

At 908, a monitoring region of interest (ROI) for contrast monitoring is optionally identified/positioned. The monitoring ROI may comprise a specific region of the patient wherein contrast level is monitored during the scan. In some examples, the monitoring ROI may be positioned outside of the area of the patient to be imaged. In other examples, the monitoring ROI may be positioned within the imaging area such that the projection data acquired for diagnostic purposes may also be used for monitoring. Thus, an operator may select the monitoring ROI based on the baseline image acquired at 906. Determining the monitoring ROI may therefore comprise receiving a selection of a monitoring ROI from an operator, for example via operator console 220. In some examples, a monitoring ROI may be not be identified/positioned. Rather, the monitoring ROI may be segmented tissue from a plurality of reconstructed images (e.g., when the tissue uptake curve signal is used to estimate the AIF/VOF curves and/or time points of interest).

At 910, a first injection of contrast agent into the patient is performed. As a non-limiting example, the contrast agent may comprise iodine. As other examples, the contrast agent may comprise an ionic contrast medium such as meglucamine diatriozoate, or a non-ionic contrast medium such as iopromide or ohexol. The contrast agent may be intravenously injected using either automatic (e.g., via an automatically-controlled power injector) or manual methods.

At 912, an injection timing of a second injection of contrast agent (I2) is initialized to a fallback timing. The fallback timing may be set to a maximum time in between bolus 1 injection end and the second injection start. In one example, this time may be set to 121 seconds (e.g., FB_postE1), but other amounts of time are within the scope of this disclosure (e.g., 120 seconds, 125 seconds, etc.). In this way, once the first contrast bolus has been administered and the first contrast scan commences, the system may be initialized with the fallback timing for the second contrast bolus as the default. Accordingly, if one or more of the bolus fenceposts cannot be identified, the second contrast bolus may be administered at the fallback timing and thus the second contrast scan will not be compromised in such a situation.

At 914, an arterial inflow function (AIF) or tissue uptake curve (TUC) signal is measured upon the first injection and the AIF or TUC signal is monitored for a signal peak (e.g., arterial peak or tissue uptake peak), F1, and/or F2. As explained above with respect to FIGS. 3-6, the AIF signal may include a first portion of an AIF curve that is measured at an arterial ROI. Depending on the scan protocol, the AIF segment may include and extend past the arterial peak (when the first contrast agent injection is a timing bolus), as shown in FIG. 4, or the AIF segment may not include the arterial peak (when the first contrast agent injection is the contrast agent injection for the first contrast scan), as shown in FIG. 5. Likewise, depending on the scan protocol, the TUC segment may include and extend past the tissue uptake peak (when the first contrast agent injection is a timing bolus), as shown in FIG. 7, or the TUC segment may not include the tissue uptake peak (when the first contrast agent injection is the contrast agent injection for the first contrast scan), as shown in FIG. 8. However, in some examples, it may be possible to continue to measure the TUC signal during the first contrast scan, and thus when the TUC is measured, an entire TUC may be generated, at least in some examples.

To measure the AIF signal or the TUC signal, a plurality of images of the monitoring ROI may be reconstructed (e.g., by image reconstructor 230) from projection data obtained by the CT system (e.g., from projection data obtained via detector array 108, which detects x-rays generated by x-ray source 104) with a relatively low x-ray dose (e.g., a tube current of 100 mAs or less). When the AIF signal is obtained, the monitoring ROI may be an artery, and when the TUC signal is obtained, the monitoring ROI may be the entire brain (although the entire head region may be imaged, and the brain may be segmented from background/other tissue after image reconstruction). The signal intensity (e.g., in HU) of the monitoring ROI/segmented tissue relative to a baseline level for each image may be determined and plotted as a function of time to arrive at the AIF signal or TUC signal. In some examples, the AIF signal may be measured from raw projection data without requiring image reconstruction to measure the AIF signal.

The AIF signal or TUC signal may be measured for a period of time that is based on the scan protocol and patient-specific contrast uptake parameters. For example, when the first contrast injection is a timing bolus, the AIF signal or TUC signal may be measured for a first, longer period of time. In such examples, the AIF signal may be measured until just after the arterial peak is reached. The rate of change in contrast level (e.g., an instantaneous rate of change or the slope of the AIF curve) may be monitored to determine when the arterial peak has been reached. For example, a positive rate of change indicates that the contrast level is increasing, while a negative rate of change indicates that the contrast level is decreasing. Once a negative rate of change is indicated for at least two successive samples (e.g., scan acquisitions) following a positive rate of change indication for at least two successive samples (e.g., scan acquisitions) during measurement of the AIF signal, it may be confirmed that the arterial peak has been reached and the measurement may be terminated. Likewise, for the TUC signal, once a negative rate of change is indicated for at least two successive samples (e.g., scan acquisitions) following a positive rate of change for at least two successive samples during measurement of the TUC signal, it may be confirmed that the tissue uptake peak has been reached and the measurement may be terminated. When the first contrast injection is the contrast injection for the first contrast scan, the AIF signal or the TUC signal may be measured for a second, shorter period of time. In such examples, the AIF signal or TUC signal may be measured until a mid-point of the arterial contrast enhancement or a mid-point of the tissue contrast enhancement, respectively, such as until a specified number of measurement samples having a positive rate of change of contrast levels has been detected and/or until the first contrast scan is initiated by an operator of the imaging system.

In still further examples, depending on the scan protocol of the first scan, the AIF or TUC signal may continue to be measured even after diagnostic acquisitions have commenced. For example, if the first contrast scan is a multiphase CTA, the monitoring ROI may be imaged between acquisitions of the mCTA during non-imaging periods of the scan protocol where the CT system may otherwise be inactive. In doing so, the estimation of the AIF/VOF curves may be improved by allowing additional AIF signal to be obtained and input to the machine learning model. If the first contrast scan is a CTP, and the TUC signal is measured, the TUC may be monitored over the entirety of the CTP.

F1 and/or F2 may be identified from the AIF or TUC signal. For example, R1, A1, and/or C1 of the first contrast injection may be estimated based on the AIF or TUC signal. Estimating the timing of R1, A1, and/or C1 may include estimating the AIF and VOF curves from the AIF or TUC signal using a machine learning model. As explained above, the AIF or TUC signal may include a measured segment of the AIF curve or the TUC that may be used as input to a model, and the model may output the estimated AIF curve and the estimated VOF curve. The model may be a suitable machine learning model, such as a decision tree, regression model, neural network, and so forth. The regression model may include a bootstrap algorithm that is trained with a dataset of N samples, where each sample includes a measured signal (whether entire AIF and VOF curves, or select features such as rate of change at the ascent of the AIF curve, AIF peak time and height, and/or AIF knee time and height) from a respective patient and identified (e.g., by an expert) ground truth, such as HU and time values for certain points of interest on the AIV and/or VOF curves (e.g., A, B, C, Q, R), such that a plurality of measured signals and corresponding ground truths from a plurality of different patients are included in the dataset. The bootstrap algorithm creates random sub-samples of the dataset with replacement to output multiple values of a desired statistic, such as a mean. The average of those multiple values provides a robust estimate of the statistic. For example, the bootstrap algorithm may be applied to determine multiple values of each of a mean time to arterial peak, a mean time to venous peak, and a mean time to venous return to baseline, with each mean value correlated to an input measured signal. In some examples, the bootstrap algorithm may be aggregated where predictions (e.g., of the means described above) from multiple decision trees may be combined to reduce variance and overfitting. Cross-validation may be performed, where the input data (e.g., training dataset) is divided into n subsets, the regression model is trained with n–1 subsets, and the remaining subset is used to test the model to avoid overfitting.

In another example, the model may be a neural network that includes artificial neurons (referred to as units or nodes) arranged in a series of layers. The input units of the neural network receive information (e.g., the AIF or TUC signal), hidden units of the network process the information, the processed information is connected on positive or negative weights, and output units of the network signal a response to the learned information. In some examples, prior knowledge is used to reduce variance and improve generalizations and training data is run through the network and used to continuously change the weight vector of the network in response to a cost function, which improves the probability of an accurate output. In other words, the neural network may comprise a plurality of nodes/layers, including an input layer that receives the AIF or TUC signal and an output layer that outputs an estimated AIF curve and an estimated VOF curve (or estimated time to arterial peak, time to venous peak, and time to venous return to baseline), with connections/weights of the layers/nodes determined based on a training dataset. The training dataset may include a plurality of pairs of data, with each pair of data including measured AIF and VOF curves and an associated AIF or TUC signal, or with each pair of data including an AIF or TUC signal and corresponding time points of interest for a plurality of patients (e.g., t_AP, t_VP, and t_VRTB).

Estimating R1 may include identifying the VRTB from the VOF curve (e.g., estimated according to the machine learning model described above). For example, the VRTB may be identified as the point on the VOF curve where the contrast level drops back below a threshold, or where the VOF curve slope switches from a negative rate of change to no change. In still other examples, the model may output the timing of the VRTB (e.g., in addition to or instead of the VOF curve). The timing of the VRTB may include a duration (e.g., in seconds) from when the first contrast injection was performed until the VRTB is estimated to occur.

Estimating A1 may include identifying the arterial enhancement (e.g., arterial ascent knee) from the AIF curve (e.g., estimated according to the machine learning model described above, or directly measured from the AIF segment). For example, A1 may be identified as the point on the AIF curve where a positive slope increases above a threshold (before peaking at B1) or where the slope switches from flat and starts increasing. In still other examples, the model may output the timing of A1 (e.g., in addition to or instead of the AIF curve). The timing of A1 may include a duration (e.g., in seconds) from when the first contrast injection was performed until A1 is estimated to occur. In certain profiles, A1 may also be used as a proxy for A2.

Estimating C1 may include identifying the arterial washout (e.g., arterial descent knee) from the AIF curve (e.g., estimated according to the machine learning model described above). For example, C1 may be identified as the point on the AIF curve where a negative slope decreases below a threshold after peaking at B1. In still other examples, the model may output the timing of C1 (e.g., in addition to or instead of the AIF curve). The timing of C1 may include a duration (e.g., in seconds) from when the first contrast injection was performed until the arterial washout is estimated to occur.

In some examples, the AIF or TUC signal may be monitored to confirm that the AIF or TUC signal includes a signal peak, as F1 and/or F2 may not be identifiable from the AIF or TUC signal. For example, some patients may have contrast enhancement kinetics where a single AIF or TUC peak is not present, which may make it challenging for the system to determine F1 and/or F2 with a reasonable level of confidence. In one example, in order to determine if the AIF or TUC signal is sufficient for detecting F1 and/or F2, a peak detector may be executed that is configured to directly detect a peak in the AIF or TUC signal and evaluate whether the detected peak is the TUC peak (e.g., time point V on FIGS. 6-8) or the AIF peak by determining if the detected peak meets one or more rules that define the TUC peak or AIF peak. For example, the peak detector may look for a peak that has a double confirm (e.g., the peak may be double confirmed when two successive acquisitions are performed, each having a lower measured HU than the detected peak). If a confirmed peak is found, the found peak is considered as an internal peak candidate (IPC). If the IPC occurs before a threshold time since the contrast injection (e.g., 14 seconds), the IPC may be discarded and the process may be repeated on the next IPC. If the IPC does not occur before the first threshold time, the IPC is further analyzed to determine if the slope of the IPC is greater than a threshold slope, such as 3 HU/s. If so, that IPC is considered a spike and is discarded. If not, the time between the ascent knee (e.g., time point U on FIGS. 6-8) and the IPC is determined. If this time is less than a second threshold time, such as 4 seconds, the IPC is considered a spike and discarded. If not, it is determined if the median HU before the IPC is greater than a threshold value, such as the IPC HU minus 2. If so, the IPC is discarded. If not, the segmented tissue (e.g., brain) volume of the image acquisition at the IPC is compared to the segmented tissue volume from the previous image acquisition. If the segmented tissue volume at the IPC is different from the previous tissue volume by an amount that is greater than a threshold (e.g., 4.25%), the IPC is discarded. If not, (and if none of these described conditions are triggered), the IPC is confirmed as the tissue peak.

Once the peak detector identifies a double-confirmed peak in the AIF or TUC signal, the AIF or TUC signal (from beginning though the double confirmed peak) may be entered into an estimator configured to identify F1 and F2 from the AIF or TUC signal. The estimator may be one of the machine learning models described above. In this way, only once the peak detector has confirmed that the AIF or TUC signal includes a signal peak (and thus is sufficient for estimating F1 and/or F2) is the AIF or TUC signal entered into the machine learning model to estimate F1 and/or F2. This may reduce processing resources by waiting until sufficient signal is available before executing the machine learning model (rather than continuously running the machine learning model with insufficient signal, until sufficient signal is obtained) and may also increase the confidence in the output of the machine learning model.

At 916, when F1 and/or F2 are identified from the AIF or TUC signal, the target I2 is computed from F1, F2, and D as defined by the scan protocol. In one example, I2 may be calculated as the sum of R1 and D. In another example, I2 may be calculated as the sum of R1 and D minus A2. In another example, I2 may be calculated as the sum of C1 and D minus A2. In another example, I2 may be calculated as the sum of E1 and D.

At 918, method 900 includes determining if the target I2 is able to be computed. For example, as explained above, the peak detector may be executed to confirm that the AIF or TUC signal includes a peak. If the peak detector is not able to identify a peak as explained above within a threshold amount of time, I2 may not be able to be computed. If the model is able to compute the target I2 (YES), method 900 proceeds to 920 to determine if the target I2 passes a sanity check. The sanity check ensures that I2 is greater than or equal to a minimum time in between the end of the first injection and the start of the second injection. As described above, the minimum time SanCh_postE1 may be 60 seconds or another suitable time. If I2 passes the sanity check (e.g., if the time between the end of the injection of the first contrast bolus and the beginning of the injection of the second contrast bolus is equal to or greater than the amount of time defined by the sanity check), (YES), then method 900 proceeds to 922 to execute the target I2 as I2. In other words, if the target I2 passes the sanity check, the second contrast bolus will be injected at the target I2. If the target I2 does not pass the sanity check (e.g., NO at 920), method 900 proceeds to 926, which will be explained below Returning to 918, if the model is unable to compute the target I2 at 918, then method 900 proceeds to 924 to determine if further analysis is no longer justified. Further analysis may be justified when the amount of elapsed time since the start of the first contrast bolus injection is less than the start of the injection of the second contrast bolus as defined by the fallback injection timing (FR_postE1). The amount of time from when the first contrast bolus is injected until arterial or tissue wash out may be 50-75 seconds or more, and thus continuing to generate and monitor the AIF or TUC signal may allow for additional AIF or TUC data to be collected, which may allow the model used to identify F1 and/or F2 to be more confident and/or accurate in the identification of F1 and/or F2. If further analysis is justified (NO at 924), then method 900 returns to 914 and continues to measure the AIF or TUC signal. However, if further analysis is no longer justified (YES at 924), then method 900 proceeds to 926 to execute the fallback injection timing as I2. Since the method is initialized to the fallback at the start of the injection, the system can perform the second injection at the fallback timing when the algorithm is unable to detect F1 and/or F2, without requiring additional input from a user or incurring additional delays.

Initialing to an acceptable fallback may be more robust than detecting that F1 and/or F2 cannot be identified and then switching to a fallback. The fallback timing may account for the worst case scenario of how long it make take for the first contrast agent bolus to wash out and may be based on population data/statistics and, in some examples, a further margin. In this way, the adaptive CT system may only move the trigger point in the forward direction (vs. fallback, based on real-time patient hemodynamic assessment) and will not move the trigger time later than the initialized fallback. In doing so, when the patient's contrast signal is usable to determine F1 and F2 such that the adaptive injection timing can be calculated, the fallback injection timing may be overridden by the adaptive injection timing.

FIG. 9B continues the flowchart of method 900 from FIG. 9A.

At 928, method 900 determines if the CT system includes a power injector. A power injector may be configured to automatically inject contrast agent to the patient. If a power injector is included, then the system may proceed to 930 to automatically inject a second bolus of contrast agent at the determined injection timing (I2). In this case, the system may determine the rate, volume, and concentration of contrast agent to inject based on the scan protocol and calculate the duration of injection to deliver the commanded amount of contrast agent. The contrast agent may be the same contrast agent injected at 910.

If a power injector is not included, method 900 proceeds to 936 to disable the scan start for the second scan until I2 to prevent inadvertent early start of the second injection. Disabling the scan start may include deactivating a scan start input on a run-time GUI, such as the run-time GUI shown in FIG. 15. In this case, a user will perform the injection manually. At 938, the scan start is activated at I2 (e.g., the scan start input on the run-time GUI may be activated thereby allowing the user to trigger start of the contrast scan) and the user is prompted to inject the second bolus at I2. For example, a countdown timer may be displayed on the display device, which may expire at I2. Once the timer expires and I2 is reached, a notification (e.g., visual, audible, and/or haptic) may be output requesting the user perform the injection.

At 932, the scan is initiated. As a non-limiting example, the scan may be a CTP scan. In another example, the scan may be a CTA scan. The second contrast scan may be carried out according to scan parameters dictated by the scan protocol, and may include adjustments to tube current, table position, frame rate, or other parameters relative to the first contrast scan.

At 934, one or more diagnostic images are reconstructed based on data acquired during the scans. For example, one or more diagnostic images may be reconstructed using known reconstruction techniques, such as filtered back projection or iterative reconstruction. Images may be constructed for each scan, e.g., CTA images and CTP images. The one or more diagnostic images may be output to a display device (e.g., display device 232) for display to an operator or a physician, to a storage medium (e.g., mass storage 218) for retrieving at a later time, and so on. Method 900 may then end.

FIG. 10A shows an example timeline 1000 of a scan protocol carried out to scan a first patient, where the scan protocol includes two contrast scans carried out according to the method 900 of FIGS. 9A and 9B. The example scan protocol depicted in timeline 1000 is an mCTA scan followed by a CTP scan. Timeline 1000 includes a first plot 1001 showing estimated contrast curves for the first patient determined from a limited scan estimation method (e.g., an aSP method as described above). As such, plot 1001 includes an estimated AIF curve 1002, an estimated VOF curve 1004, and an AIF segment 1006 that is actually measured, as explained above with respect to FIG. 5. Plot 1010 shows contrast injection events and plot 1020 shows scanning passes (also referred to as acquisitions, with the tube current for each acquisition of the CT imaging system). As used herein, a scan acquisition or pass may refer to a full gantry rotation (e.g., when the brain is being imaged) or a partial gantry rotation (e.g., when the heart is being imaged). In either case, an acquisition or pass may include the amount of gantry rotation that is needed to obtain the desired views for the anatomy/scanning protocol. Each plot is a function of time and all plots are time aligned.

At time t1, a first contrast injection 1012 is started. At the same time, imaging at the monitoring ROI (e.g., an artery) begins, with low tube current and a suitable frame rate. For example, the AIF signal may be measured with a tube current of less than 100 mAs. The AIF signal may be measured based on the detected contrast levels of the images reconstructed from time t1 to time t2. The AIF signal may be the AIF segment 1006 shown in FIG. 10A. At time t2, the operator (e.g., of the CT system) may determine that the arterial peak of the contrast enhancement is about to occur, and thus measurement of the AIF signal may stop and the first contrast scan may begin at time t3. The first contrast scan may be an mCTA and thus may include three passes of the CT imaging system at fixed intervals starting at time t3. For example, as shown, one pass may occur every eight seconds or other suitable time. The tube current during the first contrast scan may be higher than during the contrast level measurement period. The AIF signal obtained from time t1 to time t2 may be entered into a machine learning model, which may determine the estimated AIF and VOF curves shown in FIG. 10A. At the VRTB of the first contrast injection (R1), at time t4, the second contrast injection 1014 begins and the CTP scan commences. The CTP scan may be performed at a lower tube current and higher frame rate than the mCTA scan. Further, the CTP scan may include different periods with different frame rates, and may extend beyond the time shown in FIG. 10A. With respect to the method 900 presented in FIG. 9A-9B, the example shown in FIG. 10A includes a scanning protocol where F1 is R1, F2 is I2 (the injection start time of the second contrast injection), and D is zero, so that the second contrast agent injection is triggered at the estimated VRTB, as shown.

FIG. 10B shows another example timeline 1050 of a scan protocol carried out to scan a second patient where the second patient's estimated contrast curves/time points of interest cannot reliably be determined from the measured contrast curve. The example scan protocol depicted in timeline 1050 is an mCTA scan followed by a CTP scan. Timeline 1050 includes a first plot 1051 showing measured contrast levels, as explained above with respect to FIG. 5. Plot 1051 only includes an AIF segment 1052 that is actually measured, with sensing methodology explained above with respect to FIG. 5. As appreciated by plot 1051, the AIF segment 1052 does not include a distinct peak. As such, an estimated VOF curve cannot be determined, and various time points of interest, such as the venous return to baseline and/or arterial enhancement, can also not be determined. Plot 1060 shows contrast injection events and plot 1070 shows scanning passes (also referred to as acquisitions, with the tube current for each acquisition of the CT imaging system), as in FIG. 10A. Each plot is a function of time and all plots are time aligned.

At time t1, a first contrast injection 1062 is started. At the same time, imaging at the monitoring ROI (e.g., an artery) begins, with low tube current and a suitable frame rate. For example, the AIF signal may be measured with a tube current of less than 100 mAs. The AIF signal may be measured based on the detected contrast levels of the images reconstructed from data obtained during the imaging of the ROI. The AIF signal may be the AIF segment 1052 shown in FIG. 10B. However, a machine learning model may be unable to determine the estimated AIF and VOF curves, as shown in the example in FIG. 10A, due to a single AIF or TUC peak not being present. Because the system is unable to identify F1 and/or F2, the scan protocol falls back to the fallback injection time t2, which may be 131 seconds, for example. Thus, a second contrast injection 1064 is performed at t2. Accordingly, in the example shown in FIG. 10B, the patient's contrast agent kinetics are such that a reliable determination of fenceposts F1 and/or F2 cannot be made. For example, if the system cannot detect an ascent knee or a clear peak in the AIF curve or TUC, the system may determine that it cannot predict the VRTB. Thus, F1 or F2 may not be identified and the system may maintain the fallback injection timing, which in this instance may be 131 seconds after the start of the first injection at t2. Accordingly, the second contrast injection and hence second scan may start later than the example shown in FIG. 10A. However, because the system initialized the fallback timing, the mCTA and CTP scans were each still carried out in an acceptable timeframe.

Figure 11A:
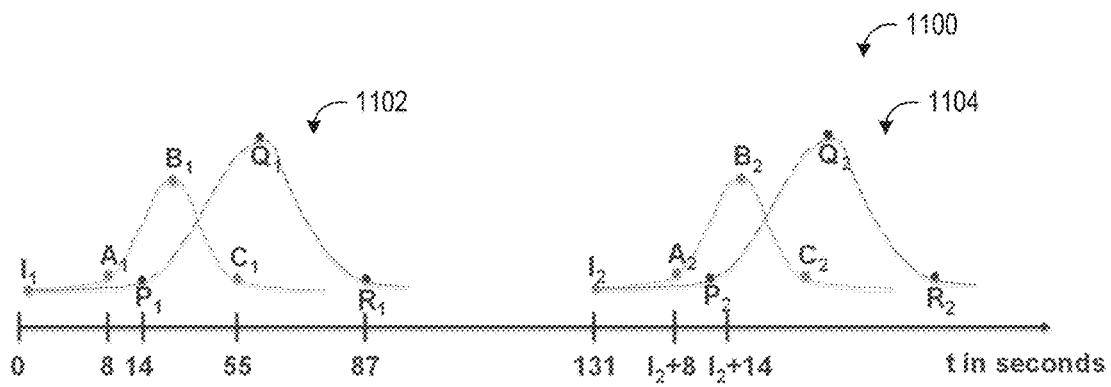
FIGS. 11A-11D show example adaptive injection timing profiles.
Figure 11B:
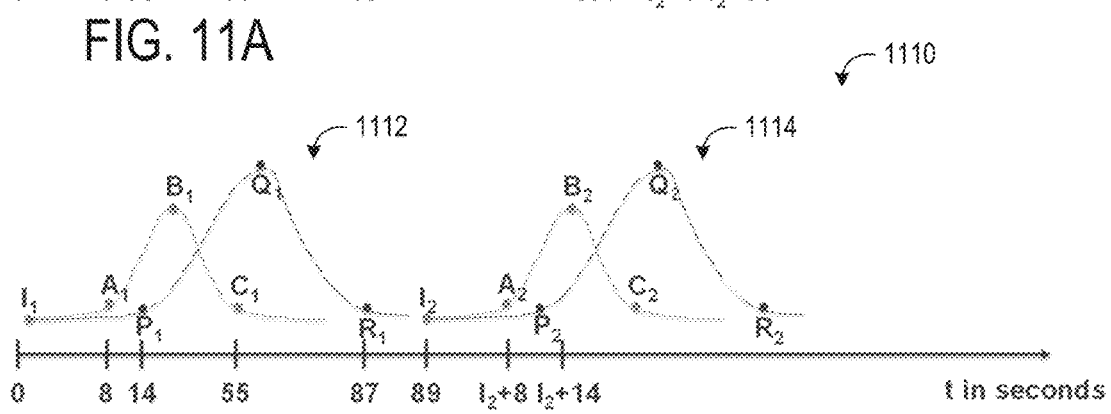
Figure 11C:
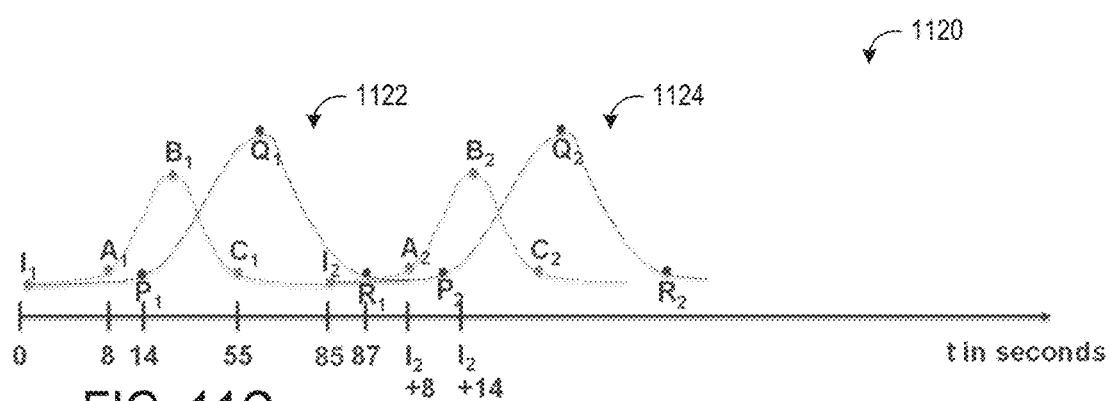
Figure 11D:
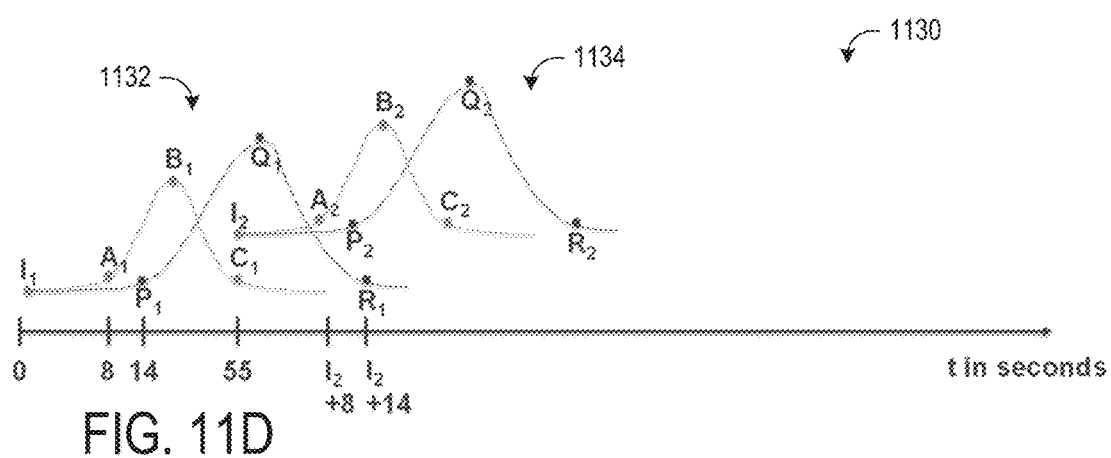

FIGS. 11A-11D show examples of modeled AIF and VOF curves for a patient administered two successive contrast injections according to a fallback injection timing (FIG. 11A), a conservative injection timing (FIG. 11B), an aggressive injection timing (FIG. 11C), and a super aggressive injection timing (FIG. 11D). In all curves, the time of first injection of contrast agent (I1) may occur at 0 seconds. Points A1, B1, and C1 refer to the start of arterial enhancement (e.g., the ascent knee), the arterial peak, and the arterial return to baseline, respectively, for a first contrast bolus. Points P1, Q1, and R1 refer to the start of venous enhancement (e.g., the venous ascent knee), the venous peak, and the venous return to baseline, respectively, for the first contrast bolus. In all examples, A1 may occur at 8 seconds, P1 may occur at 14 seconds, C1 may occur at 55 seconds, and R1 may occur at 87 seconds, as shown in curves 1102, 1112, 1122, and 1132. Point I2 refers to the time of the second injection of contrast agent (e.g., the start of the second bolus). Points A2, B2, and C2 refer to the start of arterial enhancement (e.g., the ascent knee), the arterial peak, and the arterial return to baseline, respectively, for a second contrast bolus. Points P2, Q2, and R2 refer to the start of venous enhancement (e.g., the venous ascent knee), the venous peak, and the venous return to baseline, respectively, for the second contrast bolus. Additionally, in all examples, the first injection end time (E1) is set to 10 seconds, and the fallback timing FB_postE1 is set to 121 seconds.

FIG. 11A presents a set of AIF and VOF curves for a "fallback" injection timing 1100 with the fallback injection timing (FB_postE1) set to 121 seconds. I2 thus occurs at FB_postE1 plus E1, which in this example is at 131 seconds. A2 may occur at 139 seconds (131 plus 8, or I2 plus A1), and P2 may occur at 145 seconds (131 plus 14, or I2 plus P1). The fallback injection timing may be used if the system (e.g., machine learning model as described above) cannot calculate predicted AIF and/or VOF curves, and thus provides robustness to the system.

FIG. 11B presents a set of AIF and VOF curves for a "conservative" injection profile 1120. In the conservative injection profile, the delay D may be set to 2 seconds, F1 may be R1, and F2 may be I2. Accordingly, I2 is set to occur at R1 plus D. Thus, in the second injection profile 1114, I2 occurs at 89 seconds (e.g., 2 seconds after R1, which occurs at 87 seconds), A2 may occur at 97 seconds (89 plus 8, or I2 plus A1), and P2 may occur at 103 seconds (89 plus 14, or I2 plus P1). The intent of this profile is to actuate bolus 2 injection start (I2) at bolus 1 venous washout plus the fixed delay (D) of 2 seconds.

FIG. 11C presents a set of AIF and VOF curves for an "aggressive" injection profile 1130. In the aggressive injection profile, the delay D may be set to 6 seconds, F1 may be R1, and F2 may be A2. Accordingly, I2 is set to occur at R1 (87 seconds) plus D (6 seconds) minus A1 (8 seconds). Thus, in the second injection profile 1144, I2 may then occur at 85 seconds. A2 may occur at 93 seconds (e.g., 85 plus 8, or I2 plus A1), and P2 may occur at 99 seconds (e.g., 85 plus 14, or I2 plus P1). The intent of this profile is to actuate I2 such that bolus 2 arterial enhancement start (A2) occurs at bolus 1 venous washout (R1) plus a fixed delay (D).

FIG. 11D presents a set of AIF and VOF curves for a "super aggressive" injection profile 1140. In the super aggressive injection profile, the delay D may be set to 8 seconds, F1 may be C1, and F2 may be A2. Accordingly, I2 is set to occur at C1 plus D minus A2, with A2 equal to A1. Thus, in the second injection profile 1144, I2 may occur at 55 seconds, A2 may occur at 63 seconds, and P2 may occur at 69 seconds. The intent of this profile to actuate I2 such that bolus 2 arterial enhancement start (A2) occurs at bolus 1 arterial washout (C1) plus a fixed delay (D).

FIG. 12 presents a flowchart of a method 1200 for defining an adaptive contrast scan protocol. Method 1200 is described with respect to the system and components described above with respect to FIGS. 1-2 but could be carried out with other systems/components without departing from the scope of this disclosure. Method 1200 may be carried out according to instructions stored in non-transitory memory of a computing device (e.g., computing device 216 of FIG. 2). In some examples, the scan protocol defined by method 1200 may be the scan protocol that is executed as described in method 900 of FIGS. 9A-9B. Method 1200 may include the selection/adjustment of various parameters for one or more contrast scan protocols. Thus, method 1200 may be performed in response to authenticating an authorized personnel, such as a lead technologist, radiologist, hospital administrator, etc.

At 1202, a user input specifying an adaptive scan protocol to modify is received. In some examples, the computing device may store a plurality of adaptive scan protocols, and the user input may include a selection of one of the adaptive scan protocols. The adaptive scan protocol may be a suitable contrast scan protocol, such as a CTA followed by a CTP, a CTP followed by a CTA, or another contrast scan protocol. The selected scan protocol may be specific to a particular anatomy, a particular suspected patient condition, and/or a type of patient. The user input may be received from a suitable user input device, such as the operator console 220 (which may include a keyboard, a mouse, a touchscreen, and/or another suitable input device).

At 1204, an adaptive scan protocol GUI is displayed. The adaptive scan protocol GUI may be displayed on a display device communicatively coupled to the computing device, such as display 232. The adaptive scan protocol GUI may include a number of inputs, such as entry boxes and/or dropdown menus, for selecting and entering parameters for the contrast scans. These parameters may include the type of scan to be performed, the parameters for the concentration, volume, and flow rate for the injection, and the timing fenceposts F1 and F2 with distance D, as will be explained in more detail below. An example of the adaptive scan protocol GUI is shown in FIG. 13.

At 1206, two contrast scans may be linked based on user input to the adaptive scan protocol GUI. For example, the user may enter an input indicating that a first contrast scan is to be a CTP scan and a second contrast scan is to be a CTA scan. The user may alternatively indicate that the first scan is to be a CTA scan and the second scan is to be a CTP scan. By linking the two contrast scans in the scan protocol, the two contrast scans may be performed in rapid succession when the scan protocol is executed, without a user having to separately select and execute individual scan protocols for each contrast scan at the time of scanning a patient.

At 1208, injection parameters for each scan are set based on user input to the adaptive scan protocol GUI. For example, the user may set the first contrast scan to use an injection concentration of 350 mg/mL, an injection volume of 40 mL, and an injection rate of 4 mL/s and the second contrast scan to use an injection concentration of 350 mg/mL, an injection volume of 70 mL, and an injection rate of 4 mL/s. However, the example injection parameters are exemplary, and other injection parameters may be set without departing from the scope of this disclosure, including adaptive injection parameters that are adjusted during scanning based on individual patient information.

At 1210, method 1200 determines if the user has selected adaptive timing for the second bolus (e.g., the second contrast injection). The adaptive scan protocol GUI may include a selection input (e.g., a toggle button, a dropdown menu, or other user interface control element) that may be selected or otherwise activated by the user to indicate whether the scan protocol is to include adaptive timing for the second bolus. If so (YES), method 1200 proceeds to 1212. If not (NO), method 1200 proceeds to 1224, which will be described below. In some examples, if adaptive timing is not selected, the scan protocol will set the injection timing of the second bolus to a fallback timing, which may be set by the user via the adaptive scan protocol GUI. In other examples, if adaptive timing is not selected, the scan protocol may set the second injection timing to be a fixed time that is not user-adjustable, or no timing for the second injection may be set (e.g., the operator/user of the CT system may set the timing of the second injection at the time the scan protocol is executed).

At 1212, a fallback injection timing is set by setting a fallback F1, F2, and D based on user input to the adaptive scan protocol GUI. For example, the user may enter input to the adaptive scan protocol GUI setting the fallback F1 to E1, F2 to I2, and D to 180 seconds. In some examples, the fallback injection timing may be determined by a selected injection timing profile, such as a "simple CTA" profile.

At 1214, an adaptive injection timing is set by setting an adaptive F1, F2, and D via user input. Setting the adaptive injection timing may include setting an adaptive F1, F2, and D based on user input to menu(s) of the adaptive scan protocol GUI. For example, the adaptive scan protocol GUI may include a first dropdown menu via which the user may set F1, a second dropdown menu via which the user may set F2, and an input box via which the user may enter a value for D. In some examples, the user may be presented with a limited number of options for setting the adaptive F1 and F2. For example, the first dropdown menu may only present four options for setting the adaptive F1, such as R1, C1, I1, and E1, and the second dropdown menu may only present two options for setting the adaptive F2, such as A2 and I2. In some examples, setting the adaptive F1, F2, and D may include setting an adaptive F1, F2, and D based on user selection of a profile via user input to the adaptive scan protocol GUI. For example, one or more injection timing profiles may be saved in advance, and the user may select a profile from the adaptive scan protocol GUI. Example profiles may include the profiles described above with respect to FIGS. 11A-11D or other suitable profiles. Further, in some examples, when setting the adaptive injection timing parameters (e.g., F1, F2, and D) via the adaptive scan protocol GUI, the user may save the adaptive injection timing parameters as a new profile, which may be applied to other scan protocols in the future when selected.

At 1216, a sanity check F1, F2, and D are set based on user input to the adaptive scan protocol GUI. For example, the user may set the sanity check F1 to E1, F2 to I2, and D to 30 seconds, as non-limiting examples. The sanity check may serve to ensure that a minimum delay between the first contrast injection and the second contrast injection is present, thereby avoiding injection timing errors that could result if the real-time determination of the fenceposts for an individual patient during scanning are not reliably determined. If the calculated delay falls below the sanity check, then the fallback timing will be used instead, as explained above with respect to FIGS. 9A and 9B.

At 1218, the information that is displayed via the adaptive scan protocol GUI may be updated based on the user input described above. For example, the adaptive scan protocol GUI may include a preview section that displays a visual representation of the scan protocol, where one or more generic/base contrast agent curves (e.g., an AIF curve, a VOF curve, and/or a TUC) are displayed and the selected fenceposts (e.g., the adaptive F1 and F2) and delay time between the fenceposts are displayed as part of the curves. Additional details of the adaptive scan protocol GUI, including adjustments to the preview section, are discussed below with respect to FIG. 13.

At 1220, the adaptive scan protocol is saved when indicated (e.g., in response to a user input commanding the protocol be saved). The saved protocol may be stored in mass storage 218 (with respect to FIG. 2) or within additional memory with in computing device 216 or on a network-accessible memory (e.g., the cloud, a PACS system, etc.). The saving of the scan protocol may include saving any adjustments made to the scan protocol. The scan protocol may then be retrieved at a later time and executed in order to scan a patient according to the parameters specified in the scan protocol, as explained below with respect to FIG. 14. Method 1200 may then end.

FIG. 13 shows an example adaptive scan protocol GUI 1300 that may be displayed on a display device (e.g., display 232) in response to a user request to modify an existing adaptive scan protocol or in response to a user request to establish a new adaptive scan protocol. Adaptive scan protocol GUI 1300 is a non-limiting example of the adaptive scan protocol GUI that is displayed as part of method 1200 of FIG. 12. The adaptive scan protocol GUI 1300 shown in FIG. 13 is specific to a head perfusion and angiography scan protocol (e.g., a CTP-CTA scan), but it is to be understood that a similar adaptive scan protocol GUI may be displayed in order to set parameters for other types of contrast scans.

GUI 1300 includes a scan series section 1301 that includes a plurality of user interface control inputs via which the user may define the contrast scan(s) to be performed according to the scan protocol. In the example shown in FIG. 13, the scan series section 1301 facilitates user definition of a first scan series (e.g., a first contrast scan) and a second scan series (e.g., a second contrast scan). Thus, as shown, the scan series section 1301 includes a first scan series input 1302, a first injection concentration input 1304, a first injection volume input 1306, and a first injection rate input 1308. The first scan series input 1302 may present the user with a list of scan series names (e.g., via a dropdown menu), with each name identifying a scan series having a predefined scan prescription (e.g., a scan prescription stored in memory and/or being available to be linked or imported into the scan protocol currently being defined). For example, in FIG. 13, the user has selected a CTP for the first scan series. Via the first injection concentration input 1304, the first injection volume input 1306, and the first injection rate input 1308, the user may define values for each of the contrast agent concentration, volume, and injection rate for the contrast injection of the first scan series.

The scan series section 1301 further includes a second scan series input 1310, a second injection concentration input 1312, a second injection volume input 1314, and a second injection rate input 1316. The second scan series input 1310 may present the user with the list of scan series names (e.g., via a dropdown menu), similar to the list presented via the first scan series input 1302. In FIG. 13, the user has selected a CTA for the second scan series. Via the second injection concentration input 1312, the second injection volume input 1314, and the second injection rate input 1316, the user may define values for each of the contrast agent concentration, volume, and injection rate for the contrast injection of the second scan series. Once the user has selected the desired scan series, the scan prescription for each scan series may be loaded/stored as part of the scan protocol.

The scan series section 1301 also includes an adaptive timing input 1318. When selected, activated, or otherwise turned on, the adaptive timing input 1318 may cause the timing of the second contrast injection to be determined based on the individual patient's contrast kinetics, as explained above with respect to FIGS. 9A and 9B. In response to the user selecting/activating the adaptive timing input 1318, additional sections of the GUI 1300 may become activated/available for accepting user input (e.g., a preview section 1320 and/or a timing prescription section 1330), via which the user may set the fallback timing, adaptive fenceposts and delay, and sanity check, as described below. When the adaptive timing input 1318 is not selected/activated, the additional sections maybe deactivated/unable to accept user input, at least partially. In such examples, the additional sections may change in visual appearance (e.g., go gray).

The preview section 1320 may include two sets of generic contrast curves, a first set of contrast curves 1322 and a second set of contrast curves 1324. The generic contrast curves may include generic (e.g., non-patient specific) AIF, TUC, and VOF curves and may be based on average AIF, TUC, and VOF curves for a plurality of patients, at least in some examples. The first set of contrast curves 1322 may represent average contrast curves expected to be exhibited by a patient following a first contrast injection and may include a visual indication of when (on the first set of contrast curves) F1 is to occur. The second set of contrast curves 1324 may represent average contrast curves expected to be exhibited by a patient following a second contrast injection (administered after the first contrast injection) and may include a visual indication of when (on the second set of contrast curves) F2 is to occur. Further, the preview section 1320 may include a visual indication of the delay (D) 1326 between F1 and F2. The visual indications of F1, F2, and D may change as the user prescribes the adaptive injection timing via input to the prescription section 1330, as described below.

The prescription section 1330 may include a plurality of subsections via which the user may define the fallback injection timing, the adaptive injection timing parameters, and the sanity check. The subsections include a fallback subsection 1332, an adaptive subsection 1334, and a sanity check subsection 1336. Each subsection includes a plurality of inputs via which the user may select or specify a profile and/or set F1, F2, and D. For example, the fallback subsection 1332 includes a profile input 1338, an F1 input 1340, an F2 input 1342, and a delay input 1344. Via the profile input 1338, the user may select a preset profile for setting the fallback F1, fallback F2, and fallback D. For example, the profile input 1338 may include a selectable list of preset profiles (e.g., as a dropdown menu) with each profile dictating a fallback F1, a fallback F2, and a fallback delay. The fallback profiles may be set by the manufacturer, set by an authorized user and saved in memory, and/or set at the time of setting the scan profile, as explained below.

In the example shown in FIG. 13, the user has selected the profile "Simple CTA" from the profile input 1338. As a result, the values for the fallback F1, fallback F2, and fallback D are filled automatically with values dictated by the selected profile. For example, the fallback F1 may be set to the end of the first contrast injection (E1), the fallback F2 may be set to the start of the second contrast injection (I2), and the fallback D may be set to 180 seconds. The F1 input 1340, F2 input 1342, and delay input 1344 may auto-populate with visual indications of each of the values, and each of the inputs may not be activated for accepting user input when a fallback profile is selected, at least in some examples. In other examples, if a user enters input via the F1 input 1340, F2 input 1342, and/or delay input 1344, the selected profile may automatically be switched to "custom." If the user wishes to change the fallback profile, the user may select a different profile from the profile input 1338. If the user wishes to set a fallback timing not prescribed by a preset profile, the user may select "custom" from the profile input 1338, which may result in each of the F1 input 1340, F2 input 1342, and delay input 1344 being activated so that the user may specify custom values for the fallback F1, F2, and D. In some examples, even when setting a custom fallback profile, the fenceposts available for the fallback F1 and F2 may be limited to ensure only non-contrast curve specific fenceposts are selected, e.g., the fallback F1 may be limited to the start or end of the first contrast injection and the fallback F2 may be limited to the start or the end of the second contrast injection. When the user sets a custom fallback profile, the GUI may display a save input via which the user may choose to save the custom profile as a new preset profile, for later retrieval for setting other scan protocols, at least in some examples.

The adaptive subsection 1334 includes a profile input 1346, an F1 input 1348, an F2 input 1350, and a delay input 1352. Via the profile input 1346, the user may select a preset profile for setting the adaptive F1, adaptive F2, and adaptive D. For example, the profile input 1346 may include a selectable list of preset profiles (e.g., as a dropdown menu) with each profile dictating an adaptive F1, an adaptive F2, and an adaptive delay. The adaptive profiles may be set by the manufacturer, set by an authorized user and saved in memory, and/or set at the time of setting the scan profile, as explained below.

In the example shown in FIG. 13, the user has selected the profile "Aggressive CTA" from the profile input 1346. As a result, the values for the adaptive F1, adaptive F2, and adaptive D are filled automatically with values dictated by the selected profile. For example, the adaptive F1 may be set to venous washout of the first contrast injection (R1), the adaptive F2 may be set to the arterial enhancement of the second contrast injection (A2), and the adaptive D may be set to 15 seconds. The F1 input 1346, F2 input 1348, and delay input 1350 may auto-populate with visual indications of each of the values, and each of the inputs may not be activated for accepting user input when an adaptive profile is selected. If the user wishes to change the adaptive profile, the user may select a different profile from the profile input 1346. If the user wishes to set an adaptive timing not prescribed by a preset profile, the user may select "custom" from the profile input 1346, which may result in each of the F1 input 1346, F2 input 1348, and delay input 1350 being activated so that the user may specify custom values for the adaptive F1, F2, and D, or the user may adjust one or more of the auto-filled inputs. In some examples, even when setting a custom adaptive profile, the fenceposts available for the adaptive F1 and F2 may be limited to certain fenceposts that the model/system is able to identify, e.g., the adaptive F1 may be limited to the start or end of the first contrast injection, R1, or C1, and the fallback F2 may be limited to the start or the end of the second contrast injection and A2. When the user sets a custom adaptive profile, the GUI may display a save input via which the user may choose to save the custom profile as a new preset profile, for later retrieval for setting other scan protocols, at least in some examples.

The sanity check subsection 1336 includes a profile input 1354, an F1 input 1356, an F2 input 1358, and a delay input 1360. Via the profile input 1354, the user may select a preset profile for setting the sanity check F1, sanity check F2, and sanity check D. For example, the profile input 1354 may include a selectable list of preset profiles (e.g., as a drop-down menu) with each profile dictating a sanity check F1, a sanity check F2, and a sanity check delay. The sanity check profiles may be set by the manufacturer, set by an authorized user and saved in memory, and/or set at the time of setting the scan protocol, as explained below. When a preset profile is selected, the values for the sanity check F1, sanity check F2, and sanity check D are filled automatically with values dictated by the selected profile, as described above.

In the example shown in FIG. 13, the user has selected the profile "Custom" from the profile input 1354. As a result, the user may specify the values/fenceposts for the sanity check timing. For example, the user may set the sanity check F1 via input to the F1 input 1354 (shown as being set to the end of the first contrast injection (E1)), the sanity check F2 via input to the F2 input 1358 (shown as being set to the start of the second contrast injection (I2)), and the sanity check D via input to the sanity check delay input 1360 (shown as being set to 30 seconds). In some examples, when setting a custom sanity check profile, the fenceposts available for the sanity check F1 and F2 may be limited to certain fenceposts, e.g., the start and/or end of the injections.

As explained previously, when the user sets the adaptive prescription via the adaptive subsection 1334, updates may be made to the preview section 1320, which may allow the user to visualize aspects of the adaptive scan protocol. For example, the adaptive F1 and F2 may be indicated on the respective contrast curves as well as the delay between the adaptive F1 and F2. As shown, the preview section 1320 includes an indication of F1 on the first set of contrast curves 1322, where F1 is positioned at venous washout (R1) of the first set of contrast curves 1322 due to R1 being selected as the adaptive F1 in the adaptive subsection 1334. The preview section 1320 also includes an indication of F2 on the second set of contrast curves 1324, where F2 is positioned at arterial enhancement (A2) of the second set of contrast curves 1324 due to A2 being selected as the adaptive F2 in the adaptive subsection 1334. Further, the visual indication of the adaptive delay 1326 of the preview section 1320 has been filled in with the value for the adaptive delay specified via the adaptive subsection 1334 (herein, 15 seconds).

While not shown in FIG. 13, the adaptive scan protocol GUI 1300 may include a save input that, when selected, causes the specified scan protocol to be saved in memory, so that the specified scan protocol may be executed to scan a patient when desired, as will be explained in more detail below.

FIG. 14 shows a flow chart illustrating a method 1400 for performing a contrast scan according to an adaptive contrast scan protocol. Method 1400 is described with respect to the system and components described above with respect to FIGS. 1-2 but could be carried out with other systems/components without departing from the scope of this disclosure. Method 1400 may be carried out according to instructions stored in non-transitory memory of a computing device (e.g., computing device 216 of FIG. 2). Method 1400 may include the execution of a scan protocol in order to image a patient, where the scan protocol may be an adaptive scan protocol defined/adjusted according to the method of FIG. 12. Thus, method 1400 may be performed in response to authenticating an authorized operator, such as a lead technologist, a technologist, etc.

At 1402, a user input specifying an adaptive scan protocol to execute is received. In some examples, the computing device may store a plurality of adaptive scan protocols, and the user input may include a selection of one of the adaptive scan protocols. The adaptive scan protocol may be a suitable contrast scan protocol that includes two contrast agent injections, such as a CTA followed by a CTP, a CTP followed by a CTA, or a standalone CTA, a standalone CTP, or a combined CTP and CTA with a timing bolus. In some examples, the contrast scan protocol may not include a CTA or CTP but may include another type or types of contrast scan that dictates two contrast agent injections. The selected scan protocol may be specific to a particular anatomy, a particular suspected patient condition, and/or a type of patient. The user input may be received from a suitable user input device, such as the operator console 220 (which may include a keyboard, a mouse, a touchscreen, and/or another suitable input device). In some examples, the selected scan protocol may be a scan protocol that is set/defined/adjusted according to method 1200 described above. Further, in some examples, the operator may enter a user input indicating that the scan protocol is to be executed (e.g., as opposed to modified). In other examples, the scan protocol may be executed automatically in response to the user selecting the scan protocol.

At 1404, the operator may be prompted to perform a scout scan of an imaging subject via a run-time graphical user interface (GUI). The scout scan may include a low-resolution scan that generates 2-dimensional images of the imaging subject from which the scan range/field of view of the following diagnostic scan may be set. In some examples, a notification prompting the user to perform the scout scan may be displayed as part of a run-time GUI, and the scout scan may be performed in response to a user input commanding the scout scan be executed. The run-time GUI may be displayed on a suitable display device associated with the imaging system, such as display 232. The run-time GUI may present scan information to the operator of the imaging system, such as patient information, scan parameter settings, dose information, etc., as will be explained in more detail below. In other examples, the user may command the imaging system to perform the scout scan without the imaging system prompting the user to perform the scout scan, or the scout scan may be performed automatically. In still further examples, no scout scan may be performed.

At 1406, a diagnostic scan range may be set via the run-time GUI. For example, the image(s) generated from the scout scan may be displayed via the run-time GUI along with one or more scan range overlays. The user may adjust the extent of the scan range overlays to set the diagnostic scan range. At 1408, some or all of the adaptive scan protocol GUI may be displayed within or along with the run-time GUI. Via the adaptive scan protocol GUI, the operator may view the set scan parameters for the selected scan protocol. In some examples, the operator may adjust the set scan parameters for the current scan via the adaptive scan protocol GUI, in the same manner as discussed above with respect to FIG. 12. However, if the operator adjusts any of the scan parameters, the adjustments may not be saved. In this way, one-time adjustments to the scan protocol may be made by the operator of the imaging system during a current scan, but the selected scan protocol may not be adjusted for subsequent scans.

At 1410, a first contrast scan is performed upon a first contrast injection. Performing the first contrast scan may include performing one or more acquisitions according to a scan prescription that is generated according to the selected scan protocol. The one or more acquisitions may be commenced once a contrast agent has been injected (and after a prep delay following the contrast agent injection). As a non-limiting example, the contrast agent may comprise iodine. As other examples, the contrast agent may comprise an ionic contrast medium such as meglucamine diatriozoate, or a non-ionic contrast medium such as iopromide or ohexol. The contrast agent may be intravenously injected using either automatic or manual methods. In some examples, such as when the contrast agent is injected manually (e.g., by the operator or another clinician), the operator may enter a user input indicating the contrast agent has been injected (which may notify the imaging system of when to begin acquisitions). Further, while not included in FIG. 14, some scan protocols may include a non-contrast scan of the intended/target anatomy, which may be performed before the injection of the contrast agent.

The scan prescription may include the number and timing of each acquisition, the system settings for each acquisition (e.g., x-ray source current and voltage), the scan range (e.g., scan stop and start locations) for each acquisition, table position for each acquisition, etc. The scan prescription may be determined from the scan parameters defined in the selected scan protocol and/or the scan prescription may be adjusted based on patient data. For example, if the first contrast scan is a CTP, various zones and/or phases of the scan protocol may start or end based on patient specific events, such as the peak of the patient's VOF curve or once the contrast agent has washed out of the patient. The patient data may inform on when these events will occur relative to the start of the contrast scan. The patient data may be determined from the initial acquisitions of the first contrast scan. For example, the contrast level of a specified anatomical feature (e.g., an artery) may be measured during the initial acquisitions of the contrast scan and plotted as a function of time. After a predetermined amount of time, or once a peak of a curve formed by the plotted contrast levels (or other suitable event) is detected, the measured segment of the curve may be used to predict when subsequent events are going to occur (e.g., venous peak and venous return to baseline), and the scan prescription may be updated on the fly based on the predicted time of these events. In some examples, these initial acquisitions may be of a different anatomical feature than the anatomy intended to be imaged in the diagnostic scan, and thus once the curve segment has been measured, the table supporting the imaging subject may be automatically moved to center the intended anatomy in the imaging system.

Additionally, during execution of the first contrast scan, a contrast curve of the patient, such as a tissue uptake curve (TUC), may be generated, as explained above with respect to FIGS. 6-8 and 9A-9B. The contrast curve may be used to determine when the second contrast injection is to be performed.

At 1412, a notification of the scan progress is displayed via the run-time GUI. For example, the run-time GUI may include a visual indicator of the scan progress that may change as the scan progresses. The visual indicator may include one or more progress bars, which may indicate scan progression by progressively changing in color or brightness over time (e.g., from left to right across the progress bar), and may include relative timing of each acquisition and time between each acquisition for the first contrast scan (and the second contrast scan once the second contrast scan is performed, as explained below).

At 1414, at an injection timing determined according to the scan protocol, the user is prompted to perform a second contrast agent injection, or the second contrast agent is performed automatically. The injection timing may be determined as explained above with respect to FIGS. 9A, 9B, and 12. For example, the scan protocol may include a fallback injection timing, an adaptive injection timing, and a sanity check injection timing. The scan protocol may initialize/default to the fallback timing, which may include the second contrast injection being performed a fixed amount of time after the first contrast injection, where the fixed amount of time is dictated by the scan protocol. If the patient's individual contrast kinetics may be measured (e.g., via the TUC as described above and/or based on the contrast curve segment and machine learning model-based contrast curve performed as part of the first contrast scan) before the fixed time has elapsed, the second injection timing may be moved forward in time (relative to the fallback timing) to an adaptive timing specified by the scan protocol. For example, the adaptive timing may indicate that the second contrast injection should be performed 2 seconds after the patient's venous washout/return to baseline from the first contrast injection has occurred, or another suitable adaptive timing. Further, the adaptive timing may be implemented only if the injection timing for the second contrast injection occurs at or after a minimum delay specified by the sanity check timing. In systems where an auto-injector/power injector is included, the injector may be commanded to perform the second contrast injection at the timing indicated by the scan protocol. In systems where an auto/power injector is not included, the user may be prompted (e.g., via a notification displayed as part of the run-time GUI) to perform the second contrast injection at the timing indicated by the scan protocol.

At 1416, the second contrast scan is performed. Performing the second contrast scan may include performing one or more acquisitions according to a scan prescription for the second contrast scan that is generated according to the selected scan protocol. The one or more acquisitions may be commenced once the second contrast injection has been performed (or started) (and after a prep delay following the contrast agent injection). The scan prescription may include the number and timing of each acquisition, the system settings for each acquisition (e.g., x-ray source current and voltage), the scan range (e.g., scan stop and start locations) for each acquisition, table position for each acquisition, etc. The scan prescription may be determined from the scan parameters defined in the selected scan protocol and/or the scan prescription may be adjusted based on patient data, such as based on the contrast kinetics of the patient learned during the first contrast scan. For example, if the second contrast scan is a CTA, the acquisitions of the scan protocol may start or end based on patient specific events, such as the peak of the patient's AIF. The patient data may inform on when these events will occur relative to the start of the second contrast scan. Additionally, the progress of the second contrast scan may be provided via the run-time GUI, as explained above.

In some examples, the timing of the second contrast injection and/or updated scan prescription for the first contrast scan and/or second contrast scan may be displayed via the run-time GUI. For example, after a scan prescription is adjusted or once the timing of the second contrast injection is determined, a visual representation of the scan prescription and/or timing of the second contrast injection may be displayed as part of the run-time GUI, with the visual representation showing the patient's contrast level curve (as measured during the first contrast scan), a predicted patient contrast level curve occurring after the first contrast level curve, and a delay between the two curves based on the adaptive or fallback injection timing (once determined), similar to the preview section of the adaptive scan protocol GUI of FIG. 13. At 1418, a notification may displayed via the run-time GUI once the scan is complete. Additional details about the run-time GUI are provided below with respect to FIG. 15.

At 1420, one or more reconstructed images are displayed and/or stored. For example, one or more diagnostic images may be reconstructed from the data acquired during the contrast scan using known reconstruction techniques, such as filtered back projection or iterative reconstruction. The one or more diagnostic images may be output to a display device (e.g., display device 232) for display to an operator or a physician, to a storage medium (e.g., mass storage 218) for retrieving at a later time, and so on. Method 1400 may then end.

While method 1400 is described above as being implemented on the same computing device as method 1200 described above, in some examples method 1200 may be implemented on a separate computing device, such as an edge device, a cloud computing system, a server, etc. In such examples, the adaptive scan protocol GUI may be displayed, during execution of method 1200, on a display device associated with the separate computing device. When method 1400 is executed, the selected adaptive scan protocol may be sent from the separate computing device to the computing device executing method 1400. Such a configuration may allow a lead technologist to set adaptive scan protocol settings on one separate computing device, and those protocols may be sent out to multiple, separate imaging systems in communication with the separate computing device.

FIG. 15 shows an example run-time GUI 1500 that may be displayed on a display device (e.g., display 232) in response to a user request to execute an existing adaptive scan protocol. Run-time GUI 1500 is a non-limiting example of the run-time GUI that is displayed as part of method 1400 of FIG. 14.

The run-time GUI 1500 includes a scan prescription section 1510 where information about the scan prescription for each scan of the scan protocol for the imaging subject (e.g., patient) is displayed. The scan prescription may be generated based on the selected adaptive scan protocol and, in some examples, contrast level curve information for the patient. The run-time GUI 1500 also includes a progress bar 1520 that displays the current status/progress of the contrast scan. Additionally, the run-time GUI 1500 may include a patient information section 1530, a scan information section 1540, a scan range selection section 1550, and a dose information section 1560. In the patient information section 1530, information about the imaging subject may be displayed, such as a patient name and/or ID number, patient gender, and patient position (e.g., head first/supine). In the scan information section 1540, information about the scan protocol may be displayed, such as the name of the scan protocol and the sequences/series of the scan protocol (e.g., the scout scan, the non-contrast scan, and contrast scan or scans, which as shown in FIG. 15 includes a CTP followed by a CTA). Additionally, when a sequence of the scan protocol is completed, a checkmark or other visual indicator may be displayed. The current sequence may be highlighted or otherwise visually indicated. In the scan range selection section 1550, scout images of the imaging subject may be displayed with the current scan range displayed as an overlay on the scout image(s). The scan range may be adjusted by resizing the overlay(s). In the dose information section 1560, information about the x-ray radiation dose administered to the imaging subject may be displayed, such as projected dose, total accumulated dose, etc., so that the operator of the imaging system may monitor the patient's x-ray radiation exposure.

Run-time GUI 1500 may include a series of views as the contrast scans are completed. In the view shown in FIG. 15, a user (e.g., a technologist executing the scans on the patient) is viewing scan settings/scan prescriptions before the contrast scans have commenced. Specifically, the scan prescription/settings for the CTA series of the scan protocol is being displayed. In the scan prescription section 1510, the prescription for the CTA is shown, including the scan range for the CTA, the kV and mA for the CTA, contrast agent injection parameters for the CTA, the scan type (e.g., axial versus helical), reconstruction parameters, etc. While not shown in FIG. 15, the user may view scan settings/prescription for the CTP (e.g., by selecting the CTP from the scan information section 1540).

Further, run-time GUI 1500 may display a replicate of the adaptive scan protocol GUI 1512 (e.g., as shown in FIG. 13) so that the operator is given the opportunity to confirm the settings for the current adaptive scan protocol, and if desired, change any of the settings. As an example, the operator may decide to extend the delay D between F1 and F2 to ensure that sufficient time is allowed before the second contrast injection after the subject's venous return to baseline. Some patients, such as patients with atrial fibrillation or patients that are over the age of 80, may have relatively long venous descent times, and thus contrast agent washout may occur later for these patients than other patients. Thus, the operator may conclude that the adaptive injection timing for the second contrast injection starts too early for the subject if the subject is over 80 or the operator knows the subject has atrial fibrillation, and the operator may extend the delay for that subject.

Further, the run-time GUI 1500 may include one or more user interface inputs that, when selected by the operator, confirm the scan protocol setting and/or trigger the start of the contrast scan. When the user selects or otherwise enters input indicating to confirm the settings and/or start the scan, both the first and second contrast scans (e.g., the CTP and the CTA) may commence without further user input, at least in some examples.

As each contrast scan progresses, the progress bar 1520 may change in visual appearance. For example, the progress bar 1520 may include a waveform, with each raised segment of the waveform representing an acquisition. As the scan progresses, the color of the waveform may progressively change, e.g., turning gray to blue from left to right, in sync with the scan progress.

In some examples, when the acquisitions are complete and as projection data is sent for image reconstruction/post-processing, the actual contrast level curve may be generated. In some examples, a post-scan workflow may include displaying to the operator a comparison of the estimated contrast level curve used to generate the scan prescription vs. the actual measured contrast level curve. The differences between the estimated and measured curves may be used to inform the operator of the accuracy of the curve estimates, inform the operator of any errors in the estimates that might have impacted diagnostic image quality, and/or update the curve estimation models.

In any of the methods described herein, once the time points have been estimated and the scan protocols commence based on the estimated time points, the AIF or TUC signal may continue to be measured in order to determine an actual AIF curve, VOF curve, and/or TUC. If an acquisition timed based on an estimated time point (e.g., an mCTA acquisition) is determined to have been acquired at an incorrect time, an operator may be notified so that the acquisition may be repeated at the correct time. This may include performing an additional scan, with an additional contrast agent bolus, but may reduce undue reconstruction time, as the operator may be notified before full diagnostic reconstruction has begun, rather than waiting until the diagnostic images have been reconstructed to determine that one or more scans did not produce sufficient diagnostic images. Further, in any of the methods described herein, when the acquisitions are complete and as projection data is sent for image reconstruction/post-processing, the actual AIF/VOF/TUC curves may be generated and displayed to the user as comparison of the AIF/VOF/TUC estimates used to generate the scan prescription(s) described herein versus the actual measured AIF, VOF, and/or TUC curves. The differences between the estimated and measured AIF/VOF/TUC curves may be used to inform the user of the accuracy of the AIF/VOF/TUC estimates, inform the user of any errors in the estimates that might have impacted diagnostic image quality, and/or update the machine learning estimation models.

A technical effect of the disclosure is that a second contrast injection following a first contrast injection may be timed to occur at an adaptive timing on a patient by patient basis, which may reduce the time for diagnostic imaging while maintaining the diagnostic quality of the images. A further technical effect of the disclosure is that the second contrast injection may be set to occur at a fallback timing initially, and then moved forward in time to the adaptive timing if the adaptive timing can be calculated, which may ensure that all patients are adequately scanned without imposing additional workflow steps at the time of scanning. Another technical effect of the disclosure is that cognitive load of a scan technologist at the time of scanning may be reduced by setting fallback, adaptive, and sanity check timing parameters in advance via an adaptive scan protocol GUI.

In another representation, a method includes processing acquired projection data of a first subject to measure a first contrast signal of a first contrast bolus delivered to the first subject via a first contrast injection; setting a first timing for a second contrast injection of a second contrast bolus to be delivered to the first subject to a first fallback injection timing; identifying a first adaptive injection timing for the second contrast injection based on the first contrast signal before the first fallback injection timing is reached, and in response, updating the first timing for the second contrast injection to the first adaptive injection timing and commanding initiation of the second contrast injection at the first adaptive injection timing; processing acquired projection data of a second subject to measure a second contrast signal of a third contrast bolus delivered to the second subject via a third contrast injection; setting a second timing for a fourth contrast injection of a fourth contrast bolus to be delivered to the second subject to a second fallback injection timing; not identifying a second adaptive injection timing for the fourth contrast injection based on the second contrast signal before the second fallback injection timing is reached, and in response, commanding initiation of the fourth contrast injection at the second fallback injection timing. In a first example of the method, the first fallback injection timing comprises a predetermined amount of time after commencement or completion of the first contrast injection, the second fallback injection timing comprises the predetermined amount of time after commencement or completion of the third contrast injection, and wherein each of the first fallback injection timing and the second fallback injection timing is independent of a respective contrast signal. In a second example of the method, which optionally includes the first example, the first contrast injection and the second contrast injection are performed as part of an adaptive scan protocol to image the first subject, wherein the adaptive scan protocol defines a first fencepost of the first contrast bolus, a second fencepost of the second contrast bolus, and a predetermined delay between the first fencepost and the second fencepost, and wherein the first adaptive injection timing is set so that, while carrying out the adaptive scan protocol to image the first subject, the second fencepost of the second contrast bolus follows the first fencepost of the first contrast bolus with the predetermined delay, where at least one of a first time when the first fencepost occurs and a second time when the second fencepost occurs in the first subject is identified or predicted based on the first contrast signal. In a third example of the method, which optionally includes one or both of the first and second examples, the first fencepost comprises commencement of the first contrast injection, completion of the first contrast injection, a venous return to baseline of the first contrast bolus, or an arterial washout of the first contrast bolus and the second fencepost comprises commencement of the second contrast injection or an arterial enhancement of the second contrast bolus. In a fourth example of the method, which optionally includes one or more or each of the first through third examples, the method further includes estimating an arterial inflow function (AIF) curve and/or a venous outflow function (VOF) curve for the first subject based on the first contrast signal, and identifying the venous return to baseline of the first contrast bolus, the arterial washout of the first contrast bolus, and/or the arterial enhancement of the second contrast bolus based on the estimated AIF curve and/or the estimated VOF curve. In a fifth example of the method, which optionally includes one or more or each of the first through fourth examples, identifying the first adaptive injection timing before the first fallback injection timing is reached comprises identifying the first time that first fencepost occurs and/or the second time that the second fencepost occurs in the subject based on the estimated AIF curve and/or the estimated VOF curve before the first fallback injection timing is reached. In a sixth example of the method, which optionally includes one or more or each of the first through fifth examples, identifying the first adaptive injection timing further comprises confirming that the first time and the second time occur at least a predetermined minimum amount of time apart. In a seventh example of the method, which optionally includes one or more or each of the first through sixth examples, estimating the AIF curve and/or the VOF curve includes entering the first contrast signal as input to a machine learning model trained to output the estimated AIF curve and/or VOF curve as a function of the first contrast signal.

An embodiment of a method, includes processing acquired projection data of a subject to measure a contrast signal of a first contrast bolus delivered to the subject via a first contrast injection; setting a timing for a second contrast injection of a second contrast bolus to a fallback injection timing; and responsive to identifying, based on the contrast signal, an adaptive injection timing of the subject for the second contrast injection before the fallback injection timing is reached, updating the timing for the second contrast injection to the adaptive injection timing and commanding initiation of the second contrast injection at the adaptive injection timing, otherwise commanding initiation of the second contrast injection at the fallback injection timing. In a first example of the method, the fallback injection timing comprises a predetermined amount of time after commencement or completion of the first contrast injection and wherein the fallback injection timing is independent of the contrast signal. In a second example of the method, which optionally includes the first example, the first contrast injection and the second contrast injection are performed as part of an adaptive scan protocol to image the subject, wherein the adaptive scan protocol defines a first fencepost of a response to the first contrast bolus in the subject, a second fencepost of response to the second contrast bolus in the subject, and a predetermined delay between the first fencepost and the second fencepost, and wherein the adaptive injection timing is based on the first fencepost, the second fencepost, and the predetermined delay, such that, while carrying out the adaptive scan protocol to image the subject, the second fencepost follows the first fencepost with the predetermined delay, where at least one of a first time when the first fencepost occurs and a second time when the second fencepost occurs in the subject is identified or predicted based on the contrast signal. In a third example of the method, which optionally includes one or both of the first and second examples, the first fencepost comprises commencement of the first contrast injection, completion of the first contrast injection, a venous return to baseline of the first contrast bolus, or an arterial washout of the first contrast bolus and the second fencepost comprises commencement of the second contrast injection or an arterial enhancement of the second contrast bolus. In a fourth example of the method, which optionally includes one or more or each of the first through third examples, the method further comprises estimating an arterial inflow function (AIF) curve and/or a venous outflow function (VOF) curve for the subject based on the contrast signal, and identifying the venous return to baseline of the first contrast bolus, the arterial washout of the first contrast bolus, and/or the arterial enhancement of the second contrast bolus based on the estimated AIF curve and/or the estimated VOF curve. In a fifth example of the method, which optionally includes one or more or each of the first through fourth examples, identifying the adaptive injection timing before the fallback injection timing is reached comprises identifying the first time that first fencepost occurs and/or the second time that the second fencepost occurs in the subject based on the estimated AIF curve and/or the estimated VOF curve before the fallback injection timing is reached. In a sixth example of the method, which optionally includes one or more or each of the first through fifth examples, identifying the adaptive injection timing further comprises confirming that the first time and the second time occur at least a predetermined minimum amount of time apart. In a seventh example of the method, which optionally includes one or more or each of the first through sixth examples, estimating the AIF curve and/or the VOF curve includes entering the contrast signal as input to a machine learning model trained to output the estimated AIF curve and/or VOF curve as a function of the contrast signal. In an eighth example of the method, which optionally includes one or more or each of the first through seventh examples, the acquired projection data is of an arterial region of interest (ROI) and the contrast signal comprises a segment of an arterial inflow function (AIF) curve. In a ninth example of the method, which optionally includes one or more or each of the first through eighth examples, the acquired projection data is processed to segment tissue of interest of the subject in a plurality of reconstructed images and the contrast signal comprises a segment of a tissue uptake curve measured from the segmented tissue. In a tenth example of the method, which optionally includes one or more or each of the first through ninth examples, the first contrast bolus is a timing bolus, and further comprising initiating a contrast scan of the subject upon initiation of the second contrast injection. In an eleventh example of the method, which optionally includes one or more or each of the first through tenth examples, further comprising after acquiring the projection data to measure the contrast signal, initiating a first contrast scan of the subject, and upon initiation of the second contrast injection, initiating a second contrast scan of the subject.

An embodiment of method for an imaging system includes measuring a contrast level of a first contrast bolus of a subject to generate a contrast signal, the first contrast bolus delivered to the subject via a first injection; initiating a first contrast scan of the subject with the imaging system; setting a timing for a second injection of a second contrast bolus to the subject to a fallback timing; determining when a first fencepost of the first contrast bolus and/or a second fencepost of the second contrast bolus are going to occur based at least in part on the contrast signal; overriding the fallback timing and commanding the second injection be performed at an adaptive timing based on the first fencepost and the second fencepost; and upon commencement of the second injection, initiating a second contrast scan of the subject. In a first example of the method, overriding the fallback timing and commanding the second injection be performed at the adaptive timing based on the first fencepost and the second fencepost comprises overriding the fallback timing and commanding the second injection be performed at the adaptive timing only if the contrast signal is usable to determine when the first fencepost of the first contrast bolus and/or the second fencepost of the second contrast bolus are going to occur, and further comprising if the contrast signal is not usable to determine when the first fencepost of the first contrast bolus and/or the second fencepost of the second contrast bolus are going to occur, commanding the second injection be performed at the fallback timing. In a second example of the method, which optionally includes the first example, determining when the first fencepost and/or the second fencepost are going to occur based at least in part on the contrast signal comprises determining when the first fencepost and/or the second fencepost are going to occur via a machine learning model using the contrast signal as input to the machine learning model. In a third example of the method, which optionally includes one or both of the first and second examples, commanding the second injection be performed at the adaptive timing based on the first fencepost and the second fencepost comprises calculating the adaptive timing so that, upon the second injection being performed, the second fencepost occurs a predetermined amount of time after the first fencepost. In a fourth example of the method, which optionally includes one or more or each of the first through third examples, the first fencepost comprises commencement of the first injection, completion of the first injection, a venous return to baseline of the first contrast bolus, or an arterial washout of the first contrast bolus and the second fencepost comprises commencement of the second injection or an arterial enhancement of the second contrast bolus.

An embodiment of a system includes an x-ray source that emits x-rays toward a subject to be imaged; a detector that receives the x-rays attenuated by the subject; a data acquisition system (DAS) operably connected to the detector; and a computer operably connected to the DAS and configured with instructions stored in non-transitory memory that when executed cause the computer to: upon a first contrast injection of a first contrast bolus to the subject, process projection data of the subject generated by the DAS from an output of the detector and received at the computer to measure a contrast signal of the first contrast bolus; set a timing for a second contrast injection of a second contrast bolus to a fallback injection timing; and responsive to identifying an adaptive injection timing for the second contrast injection based on the contrast signal before the fallback injection timing is reached, update the timing for the second contrast injection to the adaptive injection timing and command initiation of the second contrast injection at the adaptive injection timing, otherwise command initiation of the second contrast injection at the fallback injection timing. In a first example of the system, the fallback injection timing comprises a predetermined amount of time after commencement or completion of the first contrast injection and wherein the fallback injection timing is independent of the contrast signal. In a second example of the system, which optionally includes the first example, the first contrast injection and the second contrast injection are performed as part of an adaptive scan protocol to image the subject, wherein the adaptive scan protocol defines a first fencepost of the first contrast bolus, a second fencepost of the second contrast bolus, and a predetermined delay between the first fencepost and the second fencepost, and wherein the adaptive injection timing is set so that, while carrying out the adaptive scan protocol to image the subject, the second fencepost of the second contrast bolus follows the first fencepost of the first contrast bolus with the predetermined delay. In a third example of the system, which optionally includes one or both of the first and second examples, the instructions further cause the computer to predict a first time when the first fencepost is to occur in the subject based on the contrast signal. In a fourth example of the system, which optionally includes one or more or each of the first through third examples, the instructions further cause the computer to predict a second time when the second fencepost is to occur in the subject based on the contrast signal.

An embodiment of a method for a computing device communicatively coupled to an imaging system includes displaying an adaptive scan protocol graphical user interface (GUI) on a display device coupled to the computing device; setting one or more parameters of an adaptive timing of a second injection of a second contrast bolus of a scan protocol in response to user input to the adaptive scan protocol GUI, where the second injection follows a first injection of a first contrast bolus; updating a visual representation of the one or more parameters displayed via the adaptive scan protocol GUI in correspondence to the setting of the one or more parameters; and storing the scan protocol in memory of the computing device. In a first example of the method, the method further comprises displaying, on the display device, a run-time GUI in response to a request to execute the scan protocol, the run-time GUI including a duplicate of the adaptive scan protocol GUI. In a second example of the method, which optionally includes the first example, the method further comprises, in response to the request to execute the scan protocol, setting a first scan prescription for a first contrast scan and a second scan prescription for a second contrast scan of the imaging system based on the scan protocol and performing one or more acquisitions with the imaging system according to the first scan prescription and the second scan prescription. In a third example of the method, which optionally includes one or both of the first and second examples, the method further comprises commanding the second injection at the adaptive timing in response to the request to execute the scan protocol. In a fourth example of the method, which optionally includes one or more or each of the first through third examples, the method further comprises setting a first fallback fencepost, a second fallback fencepost, and a fallback delay of the scan protocol based on user input to the adaptive scan protocol GUI; and setting a first sanity check fencepost, a second sanity check fencepost, and a sanity check delay based on user input to the adaptive scan protocol GUI. In a fifth example of the method, which optionally includes one or more or each of the first through fourth examples, commanding the second injection at the adaptive timing in response to the request to execute the scan protocol comprises: calculating a fallback timing for the second injection based on the first fallback fencepost, the second fallback fencepost, and the fallback delay; calculating a sanity check timing based on the first sanity check fencepost, the second sanity check fencepost, and the sanity check delay; and only commanding the second injection at the adaptive timing if the adaptive timing is determined before the fallback timing and if the adaptive timing occurs after the sanity check timing, otherwise commanding the second injection at the fallback timing. In a sixth example of the method, which optionally includes one or more or each of the first through fifth examples, setting one or more parameters of the adaptive timing comprises setting a first adaptive fencepost of the first contrast bolus, a second adaptive fencepost of the second contrast bolus, and an adaptive delay between the first adaptive fencepost and the second adaptive fencepost in response to user input to the adaptive scan protocol GUI. In a seventh example of the method, which optionally includes one or more or each of the first through sixth examples, setting the first adaptive fencepost, the second adaptive fencepost, and the adaptive delay in response to user input to the adaptive scan protocol GUI comprises: displaying, via the adaptive scan protocol GUI, a first adaptive fencepost input, a second adaptive fencepost input, and an adaptive delay input; and setting the first adaptive fencepost based on user input to the first adaptive fencepost input, setting the second adaptive fencepost based on user input to the second adaptive fencepost input, and setting the adaptive delay based on user input to the adaptive delay input. In an eighth example of the method, which optionally includes one or more or each of the first through seventh examples, the first adaptive fencepost input includes a first drop-down menu including a plurality of possible first adaptive fenceposts, the plurality of possible first adaptive fenceposts including a venous return to baseline of a patient venous contrast level curve, an arterial washout of a patient arterial contrast level curve, a start of the first injection, and an end of the first injection. In a ninth example of the method, which optionally includes one or more or each of the first through eighth examples, the second adaptive fencepost input includes a second drop-down menu including a plurality of possible second adaptive fenceposts, the plurality of possible second adaptive fenceposts including an arterial enhancement of the patient arterial contrast level curve and a start of the second injection. In a tenth example of the method, which optionally includes one or more or each of the first through ninth examples, updating the visual representation of the one or more parameters displayed via the adaptive scan protocol GUI in correspondence to the setting of the one or more parameters comprises: displaying, on the adaptive scan protocol GUI, a first set of generic patient contrast level curves and a second set of generic patient contrast level curves; displaying, on the adaptive scan protocol GUI, a first visual indication of the first adaptive fencepost on the first set of generic patient contrast level curves based on the user input to the first adaptive fencepost input, a second visual indication of the second adaptive fencepost on the second set of generic patient contrast level curves based on the user input to the second adaptive fencepost input, and a third visual indication of the adaptive delay the first visual indication and the second visual indication based on the user input to the adaptive delay input.

An embodiment of a method for a computing device communicatively coupled to an imaging system includes: setting an adaptive injection timing and a fallback injection timing for a second contrast injection for imaging a patient with the imaging system based on a scan protocol, the second contrast injection following a first contrast injection; displaying, on a display device coupled to the computing device, a run-time graphical user interface (GUI), the run-time GUI including a visual representation of the adaptive injection timing; upon the first contrast injection being performed and responsive to calculating the adaptive injection timing based on a patient contrast level curve of the patient before the fallback injection timing is reached, commanding the second contrast injection at the adaptive injection timing; and performing one or more acquisitions with the imaging system according to the scan protocol. In a first example of the method, the scan protocol includes a first scan prescription for a first contrast scan and a second scan prescription for a second contrast scan, and further comprising displaying, via the run-time GUI, a scan acquisition bar that progressively notifies of a current status of each of the first scan prescription and the second scan prescription. In a second example of the method, which optionally includes the first example, the patient contrast level curve is generated after at least one acquisition of the one or more acquisitions has been performed, and wherein the adaptive injection timing is calculated once the patient contrast level curve is generated. In a third example of the method, which optionally includes one or both of the first and second examples, the method further comprises determining that the adaptive injection timing cannot be calculated before the fallback injection timing is reached, and in response, commanding the second contrast injection at the fallback injection timing.

An embodiment of a system includes a display device; a non-transitory memory storing instructions; and a processor configured to execute the instructions to: display, on the display device, an adaptive scan protocol graphical user interface (GUI); adjust one or more adaptive injection timing parameters of a scan protocol in response to user input to the adaptive scan protocol GUI to generate an adapted scan protocol; update a visual representation of the one or more adaptive injection timing parameters displayed via the adaptive scan protocol GUI in correspondence to the adjustment of the one or more adaptive injection timing parameters; store the adapted scan protocol in the non-transitory memory; responsive to a user request, execute the adapted scan protocol to image a patient, where executing the adjusted scan protocol comprises: displaying, on the display device, a run-time GUI including the visual representation of the one or more adaptive injection timing parameters, commanding an imaging system to perform one or more acquisitions according to the adjusted scan protocol after a first contrast injection has commenced, and commanding a second contrast injection at a time relative to the first contrast injection, the time based on the one or more adaptive injection timing parameters and a contrast level curve of the patient. In a first example of the system, the one or more adaptive injection timing parameters comprise a first fencepost of a first contrast bolus administered via the first contrast injection, a second fencepost of a second contrast bolus administered via the second contrast injection, and a delay between the first fencepost and the second fencepost, and wherein the contrast level curve of the patient is measured upon the first contrast injection. In a second example of the system, which optionally includes the first example, the adaptive scan protocol GUI includes a preview section that displays a first set of generic contrast level curves and a second set of generic contrast level curves and wherein the visual representation of the one or more adaptive injection timing parameters displayed via the adaptive scan protocol GUI is updated to include the first fencepost on the first set of generic contrast level curves, the second fencepost on the second set of generic contrast level curves, and the delay. In a third example of the system, which optionally includes one or both of the first and second examples, the adaptive scan protocol GUI includes a scan series section and a prescription section, the scan series section including a first plurality of inputs via which a first contrast scan and a second contrast scan are set as part of the adapted scan protocol, the prescription section including a second plurality of inputs via which the one or more adaptive injection timing parameters are set. In a fourth example of the system, which optionally includes one or more or each of the first through third examples, the prescription section includes a third plurality of inputs via which a plurality of fallback injection timing parameters are set, wherein the plurality of fallback injection timing parameters comprises a first fallback fencepost of the first contrast bolus, a second fallback fencepost of the second contrast bolus, and a fallback delay between the first fallback fencepost and the second fallback fencepost, and wherein commanding the second contrast injection at the time relative to the first contrast injection based on the one or more adaptive injection timing parameters and the contrast level curve of the patient comprises: determining a fallback injection timing relative to the first contrast injection based on the plurality of fallback injection timing parameters; if an adaptive injection timing can be determined based on the contrast level curve of the patient before the fallback injection timing is reached, commanding the second contrast injection at the adaptive injection timing; and if the adaptive injection timing cannot be determined before the fallback injection timing is reached, commanding the second contrast injection at the fallback injection timing.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
processing acquired projection data of a subject to measure a contrast signal of a first contrast bolus delivered to the subject via a first contrast injection;
setting a timing for a second contrast injection of a second contrast bolus to a fallback injection timing;
monitoring the contrast signal to identify and/or predict a signal peak, a first fencepost, and/or a second fencepost; and
responsive to identifying, before the fallback injection timing is reached, an adaptive injection timing of the subject for the second contrast injection, updating the timing for the second contrast injection to the adaptive injection timing and commanding initiation of the second contrast injection at the adaptive injection timing, otherwise commanding initiation of the second contrast injection at the fallback injection timing, wherein the adaptive injection timing is identified based on the signal peak, the first fencepost, and/or the second fencepost identified and/or predicted from the contrast signal.

2. The method of claim 1, wherein the fallback injection timing comprises a predetermined amount of time after commencement or completion of the first contrast injection and wherein the fallback injection timing is independent of the contrast signal.

3. The method of claim 1, wherein monitoring the contrast signal to identify and/or predict the signal peak, the first fencepost, and/or the second fencepost comprises monitoring the contrast signal to identify and/or predict at least the first fencepost and the second fencepost, wherein the first contrast injection and the second contrast injection are performed as part of an adaptive scan protocol to image the subject, wherein the adaptive scan protocol defines the first fencepost and the second fencepost, wherein the first fencepost is of a response to the first contrast bolus in the subject, and the second fencepost is of a response to the second contrast bolus in the subject, wherein the adaptive scan protocol further defines a predetermined delay between the first fencepost and the second fencepost, and wherein the adaptive injection timing is based on the first fencepost, the second fencepost, and the predetermined delay, such that, while carrying out the adaptive scan protocol to image the subject, the second fencepost follows the first fencepost with the predetermined delay, where at least one of a first time when the first fencepost occurs and a second time when the second fencepost occurs in the subject is identified or predicted based on the contrast signal.

4. The method of claim 3, wherein the first fencepost comprises a venous return to baseline of the first contrast bolus or an arterial washout of the first contrast bolus, and the second fencepost comprises commencement of the second contrast injection or an arterial enhancement of the second contrast bolus.

5. The method of claim 4, further comprising estimating an arterial inflow function (AIF) curve and/or a venous outflow function (VOF) curve for the subject based on the contrast signal, and identifying the venous return to baseline of the first contrast bolus, the arterial washout of the first contrast bolus, and/or the arterial enhancement of the second contrast bolus based on the estimated AIF curve and/or the estimated VOF curve.

6. The method of claim 5, wherein identifying the adaptive injection timing before the fallback injection timing is reached comprises identifying the first time that the first fencepost occurs and/or the second time that the second fencepost occurs in the subject based on the estimated AIF curve and/or the estimated VOF curve before the fallback injection timing is reached, and wherein estimating the AIF curve and/or the VOF curve includes entering the contrast signal as input to a machine learning model trained to output the estimated AIF curve and/or VOF curve as a function of the contrast signal.

7. The method of claim 6, wherein identifying the adaptive injection timing further comprises confirming that the first time and the second time occur at least a predetermined minimum amount of time apart.

8. The method of claim 1, wherein the acquired projection data is of an arterial region of interest (ROI) and the contrast signal comprises a segment of an arterial inflow function (AIF) curve.

9. The method of claim 1, wherein the acquired projection data is processed to segment tissue of interest of the subject in a plurality of reconstructed images and the contrast signal comprises a segment of a tissue uptake curve measured from the segmented tissue.

10. The method of claim 1, wherein the first contrast bolus is a timing bolus, and further comprising initiating a contrast scan of the subject upon initiation of the second contrast injection.

11. The method of claim 1, further comprising, after acquiring the projection data to measure the contrast signal, initiating a first contrast scan of the subject, and, upon initiation of the second contrast injection, initiating a second contrast scan of the subject, wherein the first contrast scan is a computed tomography perfusion scan (CTP) and the second contrast scan is a computed tomography angiography (CTA) scan.

12. A method for an imaging system, comprising:
measuring a contrast level of a first contrast bolus of a subject to generate a contrast signal, the first contrast bolus delivered to the subject via a first injection;
initiating a first contrast scan of the subject with the imaging system;
setting a timing for a second injection of a second contrast bolus to the subject to a fallback timing;
determining when a first fencepost of the first contrast bolus and/or a second fencepost of the second contrast bolus are going to occur based at least in part on the contrast signal;
overriding the fallback timing and commanding the second injection be performed at an adaptive timing based on the first fencepost and the second fencepost; and
upon commencement of the second injection, initiating a second contrast scan of the subject.

13. The method of claim 12, wherein overriding the fallback timing and commanding the second injection be performed at the adaptive timing based on the first fencepost and the second fencepost comprises overriding the fallback timing and commanding the second injection be performed at the adaptive timing only if the contrast signal is usable to determine when the first fencepost of the first contrast bolus and/or the second fencepost of the second contrast bolus are going to occur, and further comprising if the contrast signal is not usable to determine when the first fencepost of the first contrast bolus and/or the second fencepost of the second contrast bolus are going to occur, commanding the second injection be performed at the fallback timing.

14. The method of claim 12, wherein determining when the first fencepost and/or the second fencepost are going to occur based at least in part on the contrast signal comprises determining when the first fencepost and/or the second fencepost are going to occur via a machine learning model using the contrast signal as input to the machine learning model.

15. The method of claim 12, wherein commanding the second injection be performed at the adaptive timing based on the first fencepost and the second fencepost comprises calculating the adaptive timing so that, upon the second injection being performed, the second fencepost occurs a predetermined amount of time after the first fencepost.

16. The method of claim 15, wherein the first fencepost comprises commencement of the first injection, completion of the first injection, a venous return to baseline of the first contrast bolus, or an arterial washout of the first contrast bolus and the second fencepost comprises commencement of the second injection or an arterial enhancement of the second contrast bolus.

17. A system, comprising:
an x-ray source that emits x-rays toward a subject to be imaged;
a detector that receives the x-rays attenuated by the subject;
a data acquisition system (DAS) operably connected to the detector; and
a computer operably connected to the DAS and configured with instructions stored in non-transitory memory that when executed cause the computer to:
upon a first contrast injection of a first contrast bolus to the subject, process projection data of the subject generated by the DAS from an output of the detector and received at the computer to measure a contrast signal of the first contrast bolus;
set a timing for a second contrast injection of a second contrast bolus to a fallback injection timing;
monitor the contrast signal for a signal peak;
if the signal peak is identified, evaluate the contrast signal to identify a first fencepost and/or a second fencepost;
responsive to identifying the first fencepost and/or the second fencepost before the fallback injection timing is reached, update the timing for the second contrast injection to an adaptive injection timing based on the first fencepost and/or the second fencepost and command initiation of the second contrast injection at the adaptive injection timing; and
responsive to the fallback injection timing being reached before the signal peak is identified or before the first fencepost and/or the second fencepost is identified, command initiation of the second contrast injection at the fallback injection timing.

18. The system of claim 17, wherein the fallback injection timing comprises a predetermined amount of time after commencement or completion of the first contrast injection and wherein the fallback injection timing is independent of the contrast signal.

19. The system of claim 17, wherein the first contrast injection and the second contrast injection are performed as part of an adaptive scan protocol to image the subject, wherein the adaptive scan protocol defines the first fencepost, the second fencepost, and a predetermined delay between the first fencepost and the second fencepost, wherein the adaptive injection timing is set so that, while carrying out the adaptive scan protocol to image the subject, the second fencepost follows the first fencepost with the predetermined delay, and wherein the first fencepost is a response to the first contrast bolus and the second fencepost is a response to the second contrast bolus.

20. The system of claim 19, wherein the instructions further cause the computer to predict a first time when the first fencepost is to occur in the subject based on the contrast signal and/or to predict a second time when the second fencepost is to occur in the subject based on the contrast signal.

* * * * *